(12) United States Patent
Bédard et al.

(10) Patent No.: US 6,534,520 B2
(45) Date of Patent: Mar. 18, 2003

(54) ANTIVIRAL COMPOUNDS

(75) Inventors: Jean Bédard, Laval (CA); Robert Rando, Beaconsfield (CA); Jean-Francois Lavallée, Blainville (CA); Guy Falardeau, Laval (CA)

(73) Assignee: BioChem Pharma Inc., Laval (CA)

( * ) Notice: Subject to any disclaimer, the term of this patent is extended or adjusted under 35 U.S.C. 154(b) by 0 days.

(21) Appl. No.: 09/775,571

(22) Filed: Feb. 5, 2001

(65) Prior Publication Data

US 2001/0031765 A1 Oct. 18, 2001

Related U.S. Application Data

(62) Division of application No. 09/209,485, filed on Dec. 11, 1998, now Pat. No. 6,255,318.
(60) Provisional application No. 60/069,331, filed on Dec. 11, 1997.

(51) Int. Cl.7 ..................... A61K 31/435; C07D 471/04
(52) U.S. Cl. ........................................ 514/301; 546/114
(58) Field of Search ........................... 546/114; 514/301

(56) References Cited

U.S. PATENT DOCUMENTS

| | | | | |
|---|---|---|---|---|
| 4,289,524 A | * | 9/1981 | Belkind et al. ................. | 71/90 |
| 4,500,526 A | | 2/1985 | Imae et al. .................. | 514/226 |
| 5,424,431 A | * | 6/1995 | Ohta et al. ................... | 546/114 |

FOREIGN PATENT DOCUMENTS

| | | | |
|---|---|---|---|
| DE | 1620508 | * | 9/1969 |
| WO | 97/34894 | | 9/1997 |

OTHER PUBLICATIONS

V.S.R. Prasad et al.: "Formation and pyrolysis of 1–(2'–thiazolo [5,4–b] pyridyl)–5–aryltetraz oles" Synthetic Communications, vol. 20, No. 13, 1990, pp. 1983–01988, XP–002100780.
V.P.Arya et al.: "Synthesis of new heterocycles: Part X—Synthesis of Thiazolo [5–b] pyridines & certain related condensed pyridines" Indian Journal of Chemistry, vo. 11, 1973, pp. 744–746.
C. Okolo: "Studies in the heterocyclic series II. 3,6–Diazaphenothiazine sulfoxides and other potential antiparasitic and pesticidal agents" Journal of Chemical and Engineering Data, vol. 16, No. 2, 1971, pp. 244–246, XP002100782.

* cited by examiner

*Primary Examiner*—Bernard Dentz
(74) *Attorney, Agent, or Firm*—Arent Fox Kintner Plotkin & Kahn, PLLC

(57) ABSTRACT

The present invention relates to heterocyclic Compounds having antiviral activity. In particular, Compounds of formula (I):

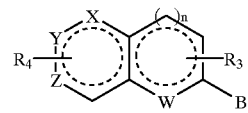

wherein B, W, X, Y, Q, $R_1$, $R_2$, $R_3$, $R_4$ and n are as defined herein, are useful in the therapy and prophylaxis of viral infection in mammals.

22 Claims, No Drawings

ANTIVIRAL COMPOUNDS

This is a Division of application Ser. No. 09/209,485 filed Dec. 11, 1998 now U.S. Pat. No. 6,255,318, The disclosure of the prior application is hereby incorporated by reference herein in its entirety which claims the benefit of U.S. Provisional Application No. 60/069,331 filed Dec. 11, 1997.

FIELD OF THE INVENTION

The present invention relates to heterocyclic compounds, and more particularly, to naphthyridine compounds and their use in therapy and prophylaxis of viral infection.

BACKGROUND OF THE INVENTION

Of the DNA viruses, the herpes group is the source of the most common viral illnesses in man. The group consists of herpes simplex virus (HSV) type I and II, varicella zoster (VZV), Epstein-Barr virus (EBV) and cytomegalovirus (CMV).

As with other herpes viruses, infection with CMV leads to a lifelong association of virus and host. Following a primary infection, virus may be shed for a number of years. Infection in otherwise healthy individuals is frequently asymptomatic, as 80% of the adult population harbor the virus in latent form. In immunocompromised individuals, such as chemotherapy patients, organ transplant patients and in particular AIDS sufferers, latent CMV can be re-activated resulting in microcephaly, hepatosplenomegaly, jaundice, convulsive seizures which may cause mental retardation, mononucleosis, retinitis and even death. In AIDS patients, CMV is a predominant cause of morbidity.

A variety of drugs have been developed to treat herpesvirus infection, including naturally occurring proteins and synthetic nucleoside analogs. For example, the natural antiviral protein, interferon, has been used in the treatment of herpesvirus infections, as have the nucleoside analogs, cytosine-arabinoside, adenine-arabinoside, iodoxyuridine and acyclovir, which is presently the treatment of choice for herpes simplex type I infection.

Unfortunately, drugs such as acyclovir that have proven effective to treat certain herpesviruses infections are not sufficiently effective to treat CMV. And, drugs currently used to treat CMV infection, such as ganciclovir (9-[(1,3-dihyroxy-2-propoxy)methyl]guanine) and foscarnet (phosphonoformic acid), lack the acceptable side effect and safety profiles of the drugs approved for treatment of other herpesviruses.

In the case of the treatments for AIDS, combination anti-HIV therapy is now the standard of care for people with HIV. There are now 11 anti-HIV drugs available by prescription. These anti-HIV drugs fall into three categories: nucleosides analogs, which include AZT, ddI, ddC, d4T and 3TC™; protease inhibitors which include indinavir, nelfinavir, saquinavir and ritonavir and non-nucleoside reverse transcriptase inhibitors (NNRTI) which include nevirapine and delavirdine. Compared to HIV, there is presently only one licensed therapy for chronic hepatitis B virus infection which is interferon. Other drugs are currently under clinical trials including lamivudine, famciclovir, lobucavir and adefovir. But many studies have shown that most patients relapse after completion of therapy and develop resistance to the drugs.

Development of resistance has recently become a major concern in the treatment of HIV and HBV infections. Resistance usually occurs when the drugs being used are not potent enough to completely stop virus replication. If the virus can reproduce at all in the presence of drugs, it has the opportunity to make changes in its structure, called mutations, until it finds one that allows it to reproduce it spite of the drugs. Once a mutation occurs, it then grows unchecked and soon is the dominant strain of the virus in the individual. The drug becomes progressively weaker against the new strain. There is also increasing concern about cross-resistance. Cross-resistance occurs when mutations causing resistance to one drug also cause resistance to another. Several studies have proven that combining two drugs delays the development of resistance to one or both drugs compared to when either drug is used alone. Other studies suggest that three-drug combinations extend this benefit even further. As a result, many people believe that the best way of preventing, or at least delaying resistance is to use multi-drug combination therapies.

The only treatment currently available for HCV infection is interferon- (IFN- ), However, according to different clinical studies, only 70% of treated patients normalize alanine aminotransferase (ALT) levels in the serum and after discontinuation of IFN, 35% to 45% of these responders relapse. In general, only 20% to 25% of patients who have long-term responses to IFN. However, pilot studies have suggested that combination treatment with IFN plus Ribavirin (RIBA) results in sustained response in the majority of patients. Different genotypes of HCV respond differently to IFN therapy, genotype 1b is more resistant to IFN therapy than type 2 and 3.

Thus, there remains a need for therapeutic and prophylactic non-nucleoside agents effective to treat viral infection. Accordingly, it is an object of the present invention to provide a method of inhibiting viral replication in a mammal. It is also an object of the present invention to provide compounds and pharmaceutical compositions useful for inhibiting viral replication in a mammal.

SUMMARY OF THE INVENTION

In one aspect, the present invention provides a method of inhibiting viral replication other than cytomegalovirus (CMV)in a mammal comprising administering to said mammal an anti-viral amount of a compound of formula (I):

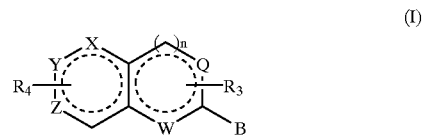

wherein

W is selected from CH, $CR_3$, $CH_2$, C=O, $CHR_3$, N and $NR_5$; one of X, Y, and Z is N or $NR_5$ while the other two are independently selected from CH, $CR_4$, $CH_2$, C=O and $CHR_4$;

Q is selected from CH, $CR_3$, $CH_2$, C=O, $CHR_3$, N, $NR_5$, O or S;

B is selected from the group consisting of;

(II)

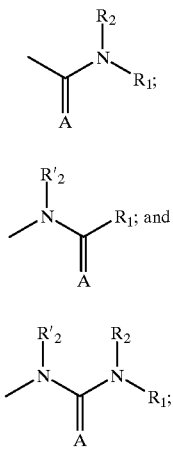

(III)

(IV)

wherein;
A is O, N or S;
$R_1$ is selected from:
  $C_{1-6}$ alkyl, $C_{2-6}$ alkenyl or $C_{3-7}$ cycloalkyl optionally substituted with OH, halogen, amino, carboxyl, or saturated or unsaturated $C_{3-10}$ (carbocycle or heterocycle) optionally substituted with OH, halogen, amino, mercapto, carboxy, $C_{1-4}$ (alkyl, alkoxy, alkylthio, acyl, acyloxy or alkoxycarbonyl) optionally substituted with OH, halogen, amino or $C_{1-4}$ alkoxy;
  $C_{3-7}$ cycloalkyl fused to $C_{6-10}$ aryl optionally substituted with OH, halogen, amino, mercapto, carboxy, $C_{1-4}$ (alkyl, alkoxy, alkylthio, acyl, acyloxy or alkoxycarbonyl) optionally substituted with OH, halogen, amino or $C_{1-4}$ alkoxy; and
  saturated or unsaturated $C_{3-10}$ (carbocycle or heterocycle) optionally substituted with OH, halogen, amino, mercapto, carboxy, $C_{1-4}$ (alkyl, alkoxy, alkylthio, acyl, acyloxy or alkoxycarbonyl) optionally substituted with OH, halogen, amino or $C_{1-4}$ alkoxy;
$R_2$ and $R'_2$ are idependently selected from H, or $C_{1-4}$ alkyl or $R_1$ and $R_2$ together form a saturated or unsaturated 5 or 6 member heterocycle optionally fused to $C_{6-10}$ aryl or heteroaryl;
$R_3$ and $R_4$ are independently selected from H, OH, halogen, amino, cyano, $C_{1-6}$ (alkyl, alkoxy, acyl, acyloxy or alkoxycarbonyl), $C_{2-6}$ alkenyl optionally substituted with OH, halogen, amino or $C_{1-4}$ alkoxy, and saturated or unsaturated $C_{3-10}$ (carbocycle or heterocycle) optionally substituted with OH, halogen, amino, mercapto, $C_{1-4}$ alkylthio, $C_{1-4}$ alkoxycarbonyl, halo-substituted $C_{1-4}$ alkyl or halo-substituted $C_{1-4}$ alkoxy, $C_{1-4}$ alkyl, $C_{1-4}$ alkoxy or carboxy;
$R_5$ is H, $C_{1-6}$ alkyl or $C_{1-6}$ acyl optionally substituted with OH, halogen, amino or $C_{1-4}$ alkoxy; and
n is 0, 1 or 2.

In yet another aspect of the invention, there is provided viral (including CMV) inhibiting compounds and pharmaceutically acceptable salts thereof according to formula (I) wherein Q is selected from S, O, N and $NR_5$.

DETAILED DESCRIPTION OF THE INVENTION

In one aspect, the present invention provides a method of inhibiting viral replication in a mammal comprising administering to said mammal an replication inhibiting amount of a compound of formula (I):

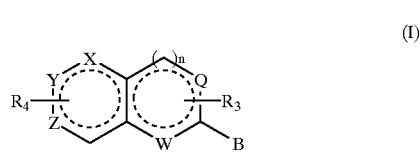

(I)

wherein W, X, Y, Q, Z, B, $R_1$ to $R_4$ and n are defined herein.

In yet another aspect of the invention, there is provided viral replication inhibiting compounds and pharmaceutically acceptable salts thereof according to formula (V):

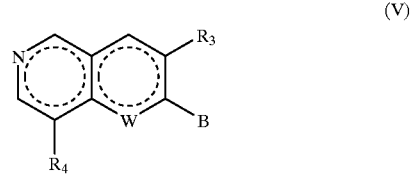

(V)

Wherein B, W, $R_3$ and $R_4$ are defined herein.

In yet another aspect of the invention, there is provided viral replication inhibiting compounds and pharmaceutically acceptable salts thereof according to formula (VI):

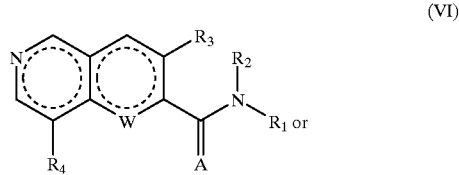

(VI)

(VII)

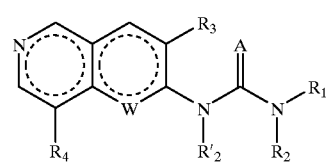

Wherein A, W, $R_1$, $R_2$, $R_3$ and $R_4$ are defined herein.

In yet another aspect of the invention, there is provided viral inhibiting compounds and pharmaceutically acceptable salts thereof according to formula (VIII):

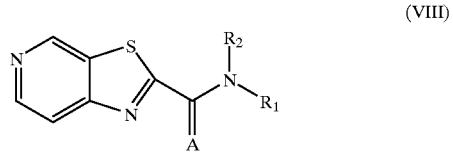

(VIII)

Wherein A, $R_1$ and $R_2$ are defined below

The term "alkyl" as used throughout the specification refers to a saturated carbon chain which may be straight or branched. Similarly the term "alkenyl" is a straight or branched carbon chain but incorporates unsaturated carbon atoms. For convenience however, the terms "alkoxy", "alkylthio", "acyl", "acyloxy" and "alkoxycarbonyl" refer to chains that are either saturated or unsaturated and may also be straight or branched. Where indicated, any of the above mentioned chains may have various substituents. It is understood that there may be one or more substituents unless otherwise specified.

The term "carbocycle" refers to a cyclic carbon chain or ring which is saturated or unsaturated. A "heterocycle" is a ring incorporating heteroatoms selected from N, O and S in place of carbon. Unsaturated carbocycles and heterocycles may be aromatic i.e. aryl such as phenyl or naphthyl, or heteroaryl such as pyridine or quinoline. Where indicated, any of the above mentioned rings may have various substitutions. It is understood that there may be one or more substituents unless otherwise specified.

The term "aryl" is an unsaturated carbocylce ring(s) of 6 to 16 carbon atoms. A "heteroaryl" is a unsaturated carbocylce ring(s) of 6 to 16 carbon atoms incorporating at least one heteroatom selected from N, O and S in place of carbon.

The term "amino" includes primary amines i.e. $NH_2$, secondary amines i.e. NHR, or tertiary amines i.e. $N(R)_2$ wherein R is $C_{1-4}$ alkyl. Also encompassed by the term are quaternary amines such as $NH_3^+$.

In methods of the present invention, viral replication is inhibited by administering compounds of formula (I), (V), (VI) (VII) and (VIII) as shown above, wherein: W is selected from CH, $CR_3$, $CH_2$, C=O, $CHR_3$, N and $NR_5$; and one of X, Y, and Z is N or $NR_5$ while the other two are independently selected from CH, $CR_4$, $CH_2$, C=O and $CHR_4$. It will be appreciated that the heterobicyclic compounds of the invention may be saturated, unsaturated or partially unsaturated and that W, X, Y and Z will have the appropriate valency for each condition. For example, when the rings are unsaturated, W may be N, CH or $CR_3$. And conversely, when the rings are saturated W may be $CH_2$, C=O, $CHR_3$, NH or $NR_5$. The same principle applies for X, Y and Z.

In a preferred embodiment n is 1.

In a preferred embodiment W is N or $NR_5$;

In a preferred embodiment X is N or $NR_5$, while Y and Z are independently CH, $CR_4$, $CH_2$, C=O or $CHR_4$.

In a preferred embodiment Y is N or $NR_5$, while X and Z are independently CH, $CR_4$, $CH_2$, C=O or $CHR_4$.

In a preferred embodiment Z is N or $NR_5$, while X and Y are independently CH, $CR_4$, $CH_2$, C=O or $CHR_4$.

In a preferred embodiment Q is CH, $CHR_5$.

In a preferred embodiment Q is S, O, N or $NR_5$.

In a preferred embodiment the heterobicyclic ring incorporating W, X, Y and Z is unsaturated.

In a particularly preferred embodiment, W and Y are independently N or $NR_5$ while X and Z are independently CH, $CR_4$, $CH_2$, C=O or $CHR_4$.

In a particularly preferred embodiment, W and Y are both N while X and Z are CH or $CR_4$ and the heterobicyclic ring is unsaturated.

In a most preferred embodiment, W and Y are both N while X and Z are CH or $CR_4$, the heterobicyclic ring is unsaturated and n is 1, thereby forming a 1,6-naphthyridine ring.

In a particularly preferred embodiment, Y is N or $NR_5$, W is CH or $CR_4$, while X and Z are independently CH, $CR_4$, $CH_2$, C=O or $CHR_4$.

In a particularly preferred embodiment, Y is N and W is CH or $CHR_4$ while X and Z are CH or $CR_4$ and the heterobicyclic ring is unsaturated.

In a most preferred embodiment, Y is N, W is $CH_2$ while X and Z are CH or $CR_4$, the left heterocyclic ring containing X, Y and Z is unsaturated, Q is $CH_2$ and n is 1, thereby forming a dihydroisoquinoline ring.

In another most preferred embodiment, W and Y are both N or $NR_5$ while X and Z are CH or $CR_4$, the left heterocyclic ring containing X, Y and Z is unsaturated, Q is S and n is 0, thereby forming a thiazolo[5,4-c]pyridine ring.

In a preferred embodiment, A is O.

$R_1$ is selected from:

$C_{1-6}$ alkyl, $C_{2-6}$ alkenyl or $C_{3-7}$ cycloalkyl optionally substituted with OH, halogen, amino, carboxyl or saturated or unsaturated $C_{3-10}$ (carbocycle or heterocycle) optionally substituted with OH, halogen, amino, mercapto, carboxy, $C_{1-4}$ (alkyl, alkoxy, alkylthio, acyl, acyloxy or alkoxycarbonyl) optionally substituted with OH, halogen, amino or $C_{1-4}$ alkoxy;

$C_{3-7}$ cycloalkyl fused to $C_{6-10}$ aryl optionally substituted with OH, halogen, amino, mercapto, carboxy, $C_{1-4}$ (alkyl, alkoxy, alkylthio, acyl, acyloxy or alkoxycarbonyl) optionally substituted with OH, halogen, amino or $C_{1-4}$ alkoxy; and saturated or unsaturated $C_{3-10}$ (carbocycle or heterocycle) optionally substituted with OH, halogen, amino, mercapto, carboxy, $C_{1-4}$ (alkyl, alkoxy, alkylthio, acyl, acyloxy or alkoxycarbonyl) optionally substituted with OH, halogen, amino or $C_{1-4}$ alkoxy.

In a preferred embodiment $R_1$ is $C_{2-6}$ alkenyl; $C_{1-6}$ alkyl or $C_{3-7}$ cycloalkyl substituted with a 6 member aryl or heteroaryl or cycloalkyl ring optionally substituted with halogen, hydroxy, $C_{1-4}$ alkyl, $C_{1-4}$ alkoxy, $C_{1-4}$ alkylthio, $C_{1-4}$ alkoxycarbonyl, halo-substituted $C_{1-4}$ alkyl or halo-substituted $C_{1-4}$ alkoxy; and $C_{3-7}$ cycloalkyl fused to a 6 member aryl or heteroaryl ring optionally substituted with halogen, hydroxy, $C_{1-4}$ alkyl, $C_{1-4}$ alkoxy, $C_{1-4}$ alkylthio, $C_{1-4}$ alkoxycarbonyl or halo-substituted $C_{1-4}$ alkyl.

In an alternative embodiment $R_1$ is an unsaturated $C_{3-10}$ (carbocycle or heterocycle) optionally substituted with OH, halogen, amino, mercapto, carboxy, $C_{1-4}$ (alkyl, alkoxy, alkylthio, acyl, acyloxy or alkoxycarbonyl) optionally substituted with OH, halogen, amino or $C_{1-4}$ alkoxy.

In a particularly preferred embodiment, $R_1$ is benzyl, pyridinylmethyl or cyclohexylmethyl optionally substituted with one or two substituents selected from hydroxy; amino, in particular $NH_2$ or $NH_3^+$; $C_{1-4}$ alkyl, in particular methyl; halogen, in particular fluoro, chloro or bromo; $C_{1-4}$ alkoxy, in particular methoxy or ethoxy; $C_{1-4}$ alkoxycarbonyl, in particular methoxycarbonyl; $C_{1-4}$ alkylthio, in particular methylthio; $C_{1-4}$ halo-substituted alkyl, in particular trifluoromethyl. More particularly preferred, $R_1$ is benzyl optionally mono or di-substituted at the 2, 3, 5 or 6 positions of the ring and most preferably at the 2 and/or 6 positions with methyl, methoxy, ethoxy, hydroxy, fluoro, bromo, chloro, methoxycarbonyl, methylthio, trifluoromethyl, trifluoromethoxy, $NH_2$ or $NH_3^+Cl^-$. In an even more preferred embodiment, $R_1$ is benzyl optionally substituted at the 2-position with fluoro, chloro, bromo, methyl, methoxy, ethoxy, methoxycarbonyl, trifluoromethyl or $NH3^+Cl^-$.

In another particularly preferred embodiment, $R_1$ is $C_{3-7}$ cycloalkyl substituted with phenyl which is optionally substituted with one or two substituents selected from hydroxy, amino, $C_{1-4}$ alkyl, halogen, $C_{1-4}$ alkoxy, $C_{1-4}$ alkoxycarbonyl, $C_{1-4}$ alkylthio or $C_{1-4}$ halo-substituted alkyl. More particularly preferred, the $C_{3-7}$ cycloalkyl is cyclopropyl.

In another particularly preferred embodiment, $R_1$ is $C_{3-7}$ cycloalkyl fused to phenyl which is optionally substituted with one or two substituents selected from hydroxy, amino, $C_{1-4}$ alkyl, halogen, $C_{1-4}$ alkoxy, $C_{1-4}$ alkoxycarbonyl, $C_{1-4}$ alkylthio or $C_{1-4}$ halo-substituted alkyl. More particularly preferred, the $C_{3-7}$ cycloalkyl is cyclopentyl or cyclohexyl.

$R_2$ and $R'_2$ are independently H, $C_{1-4}$ alkyl or $R_1$ and $R_2$ together form a saturated or unsaturated 5 or 6 member heterocycle optionally fused to $C_{6-10}$ aryl or heteroaryl. In a preferred embodiment $R_2$ is H or methyl and most preferably H. $R'_2$ is H or methyl and most preferably H.

In another preferred embodiment $R_2$ together with $R_1$ form a saturated or unsaturated 5 or 6 member heterocycle optionally fused to $C_{6-10}$ aryl or heteroaryl. Suitable 5 or 6 member heterocycles include piperidine, piperazine, morpholine, pyrrole, pyrazole and imidazole. These may be fused to a $C_{6-10}$ aryl or heteroaryl to give suitable bicyclic rings such as indole, purine, benzimidazole, quinoline or isoquinoline.

Preferably $R_3$ and $R_4$ are independently selected from H, OH, halogen, amino, cyano, $C_{1-6}$ (alkyl, alkoxy, acyl, acyloxy or alkoxycarbonyl) optionally substituted with OH, halogen, amino or $C_{1-4}$ alkoxy, and saturated or unsaturated $C_{3-10}$ (carbocycle or heterocycle) optionally substituted with OH, halogen, amino, mercapto, $C_{1-4}$ alkylthio, $C_{1-4}$ alkoxycarbonyl, halo-substituted $C_{1-4}$ alkyl or halo-substituted $C_{1-4}$ alkoxy, $C_{1-4}$ alkyl, $C_{1-4}$ alkoxy or carboxy.

$R_3$ and $R_4$ are independently selected from H, OH, halogen, amino, cyano and $C_{1-6}$ (alkyl, , alkoxy, acyl, acyloxy and alkoxycarbonyl) $C_{2-6}$ alkenyl optionally substituted with OH, halogen, amino or $C_{1-4}$ alkoxy. It is appreciated that the ring incorporating X, Y and Z, may be substituted with one to four substituents $R_4$ while the ring incorporating W may be substituted with one to three substituents $R_3$.

Preferably $R_3$ and $R_4$ are independently selected from H, OH, halogen, amino, cyano and $C_{1-6}$ (alkyl, alkoxy, acyl, acyloxy and alkoxycarbonyl) optionally substituted with OH, halogen, amino or $C_{1-4}$ alkoxy.

$R_3$ and $R_4$ are independently saturated or unsaturated $C_{3-10}$ (carbocycle or heterocycle) optionally substituted with OH, halogen, amino, mercapto, $C_{1-4}$ alkyl, $C_{1-4}$ alkoxy or carboxy.

In an alternative embodiment, $R_3$ and $R_4$ are independently 6 member aryl or heteroaryl or cycloalkyl ring optionally substituted with halogen, hydroxy, $C_{1-4}$ alkyl, $C_{1-4}$ alkoxy.

In an alternative embodiment, $R_4$ is a 6 member aryl or heteroaryl or cycloalkyl ring optionally substituted with halogen, hydroxy, $C_{1-4}$ alkyl, $C_{1-4}$ alkoxy. In a further embodiment, $R_4$ is a 6 membered heteroaryl. In a further embodiment, $R_4$ is pyridyl.

In a preferred embodiment, there is one $R_3$ substituent which is selected from H; OH; halogen, in particular fluoro or chloro; and $C_{1-4}$ alkoxy, in particular methoxy or ethoxy. More preferably, $R_3$ is H, chloro, hydroxy or methoxy and most preferably H.

In a preferred embodiment, $R_4$ is selected from H, halogen, amino, OH, $C_{1-6}$ (alkyl, alkoxy, acyl, acyloxy and alkoxycarbonyl) optionally substituted with OH, halogen or amino. Preferably, there is one or two $R_4$ substituents and most preferably there is one $R_4$ substituent.

In a more preferred embodiment $R_4$ is amino.
In a more preferred embodiment $R_4$ is $C_{1-4}$ aminoalkyl.
In a more preferred embodiment $R_4$ is OH.
In a more preferred embodiment $R_4$ is halogen.
In a more preferred embodiment $R_4$ is methoxy.
In a more preferred embodiment $R_4$ is vinyl.
In a most preferred embodiment $R_4$ is H.

$R_5$ is H, $C_{1-6}$ alkyl or acyl optionally substituted with OH, halogen, amino or $C_{1-4}$ alkoxy.

In a preferred embodiment $R_5$ is H.
In a preferred embodiment $R_5$ is $C_{1-4}$ alkyl and more preferably methyl.
In a preferred embodiment $R_5$ is $C_{1-4}$ alkyl substituted with amino and more preferably methyl or ethyl substituted with $NH_2$.
In a preferred embodiment $R_5$ is $C_{1-4}$ acyl and more preferably ethanoyl.
In a preferred embodiment $R_5$ is $C_{1-4}$ acyl substituted with amino and more preferably ethanoyl substituted with $NH_2$.

Preferred compounds of the invention include those in table 1.

TABLE 1

| No. | Structure | Name |
|---|---|---|
| #1 | 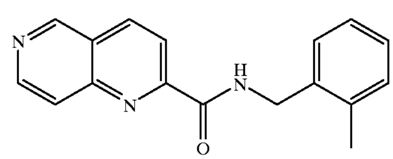 | N-(2-methylbenzyl)-2-(1,6)naphthyridinecarboxamide |
| #2 | 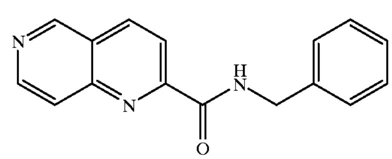 | N-benzyl-2-(1,6)naphthyridinecarboxamide |
| #3 | 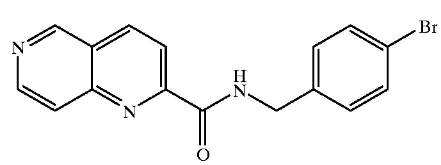 | N-(4-bromobenzyl)-2-(1,6)naphthyridinecarboxamide |

TABLE 1-continued

| No. | Structure | Name |
|---|---|---|
| #4 | 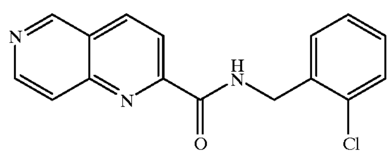 | N-(2-chlorobenzyl)-2-(1,6)naphthyridinecarboxamide |
| #5 | 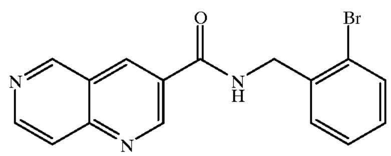 | N-(2-bromobenzyl)-2-(1,6)naphthyridinecarboxamide |
| #6 | 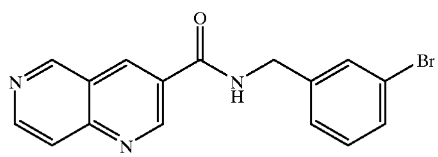 | N-(3-bromobenzyl)-2-(1,6)naphthyridinecarboxamide |
| #7 | 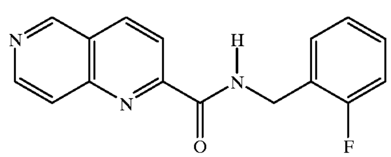 | N-(2-fluorobenzyl)-2-(1,6)naphthyridinecarboxamide |
| #8 | 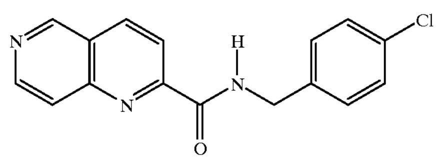 | N-(4-chlorobenzyl)-2-(1,6)naphthyridinecarboxamide |
| #9 | 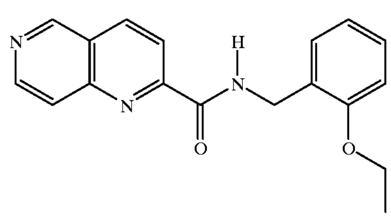 | N-(2-ethyloxybenzyl)-2-(1,6)naphthyridinecarboxamide |
| #12 | 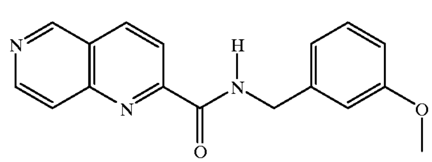 | N-(3-methoxybenzyl)-2-(1,6)naphthyridinecarboxamide |
| #13 | 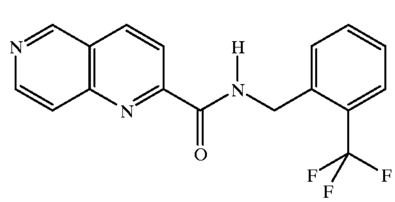 | N-(2-trifluoromethylbenzyl)-2-(1,6)naphthyridinecarboxamide |

TABLE 1-continued

| No. | Structure | Name |
|---|---|---|
| #14 | 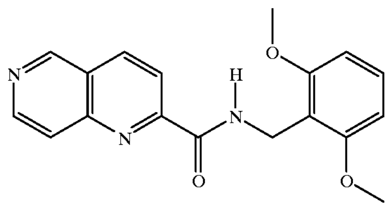 | N-(2,6-dimethoxybenzyl)-2-(1,6)naphthyridinecarboxamide |
| #15 | 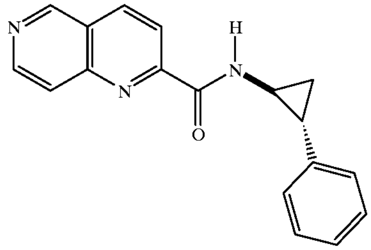 | [1,6]naphthyridine-2-carboxylic acid (trans-2-phenyl-cyclopropyl)-amide |
| | | |
| #16 | 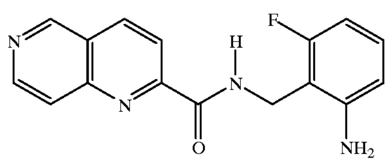 | N-(2-fluoro-5-aminobenzyl)-2-(1,6)naphthyridinecarboxamide |
| #17 | 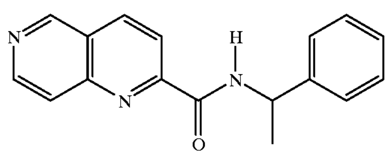 | [1,6]naphthyridine-2-carboxylic acid (1-phenyl-ethyl) amide |
| #18 | 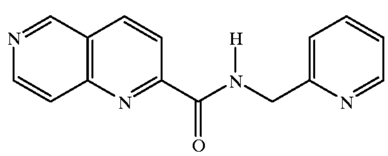 | [1,6]naphthyridine-2-carboxylic acid (pyridine-2-ylmethyl) amide |
| #19 | 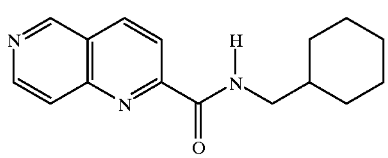 | [1,6]naphthyridine-2-carboxylic acid cyclohexylmethyl-amide |
| #20 | 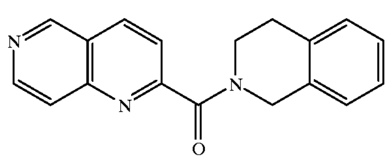 | (3,4-dihydro-1H-isoquinolin-2-yl)-[1,6]naphthyridin-2-yl-methanone |

TABLE 1-continued

| No. | Structure | Name |
|---|---|---|
| #21 | 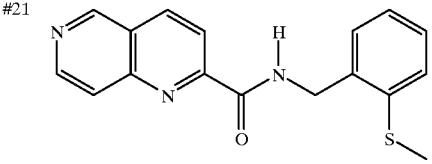 | N-(2-methylthiobenzyl)-2-(1,6)naphthyridinecarboxamide |
| #22 | 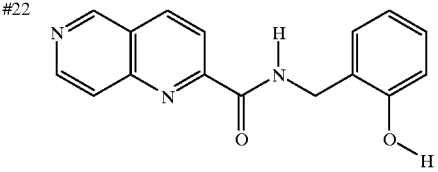 | N-(2-hydroxybenzyl)-2-(1,6)naphthyridinecarboxamide |
| #23 | 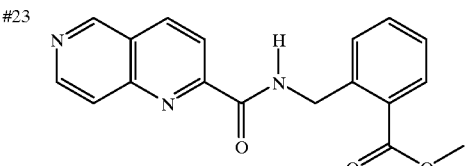 | N-(2-methoxycarbonylbenzyl)-2-(1,6)naphthyridinecarboxamide |
| #24 | 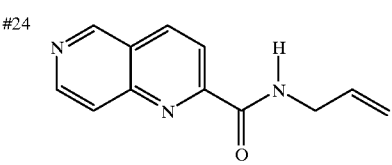 | (1,6)naphthyridine-2-carboxylic acid allylamide |
| #25 | 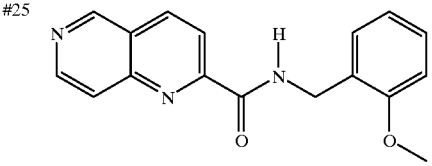 | N-(2-methoxybenzyl)-2-(1,6)naphthyridinecarboxamide |
| #26 | 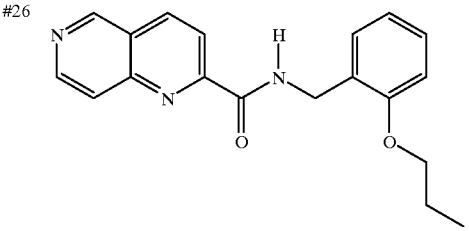 | N-(2-propoxybenzyl)-2-[1,6]naphthyridine-2-carboxamide |
| #32 | 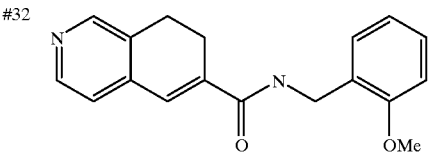 | 7,8-dihydroisoquinolin-6-carboxylic acid 2'-methoxybenzylamide |

TABLE 1-continued

| No. | Structure | Name |
|---|---|---|
| #33 | 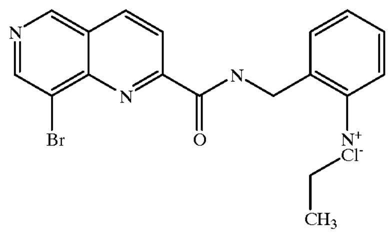 | 8-bromo-[1,6]naphthyridine-2-carboxylic acid (2-N-ethylaminobenzylamine) |
| #34 | 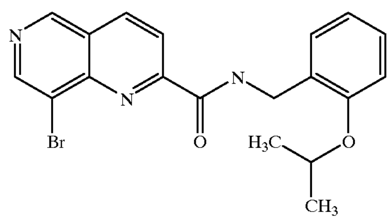 | 8-bromo-[1,6]naphthyridine-2-carboxylic acid (2-isopropoxybenzylamine) |
| #35 | 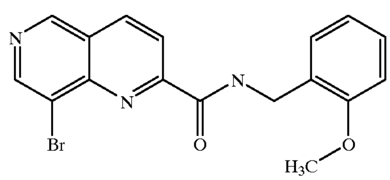 | 8-bromo-[1,6]naphthyridine-2-carboxylic acid (2-methoxybenzylamine) |
| #40 | 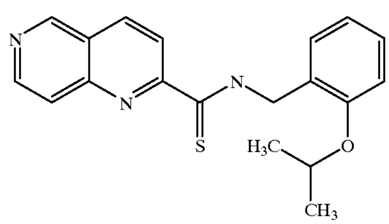 | [1,6]Naphthyridine-2-thiocarboxylic acid-2-isopropoxybenzylamine; |
| #41 | 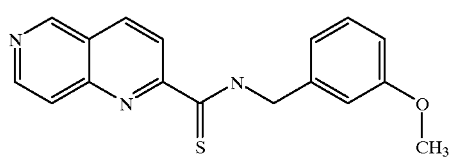 | [1,6]Naphthyridine-2-thiocarboxylic acid-3-methoxybenzylamine; |
| #46 | 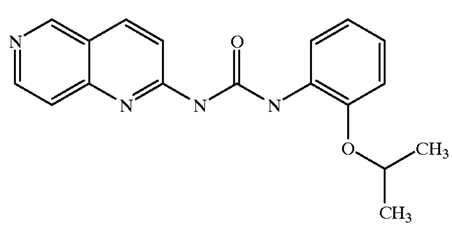 | 1-(2-iso-propoxy-phenyl)-3-[1,6]naphthyridin-2-yl-urea; |
| #47 | 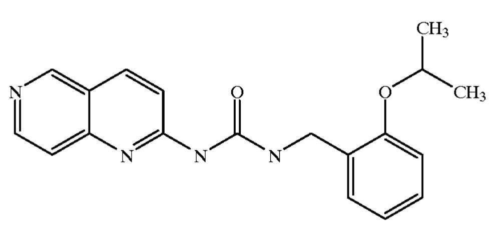 | 1-(2-iso-propoxybenzyl)-3-[1,6]naphthyridin-2-yl-urea; |

TABLE 1-continued

| No. | Structure | Name |
|-----|-----------|------|
| #48 | 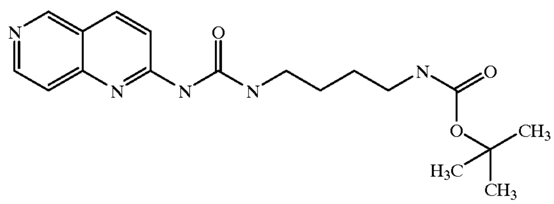 | 1-(N-boc-4-aminobutyl)-3-[1,6]naphthyridin-2-yl-urea; |
| #49 | 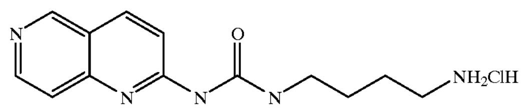 | 1-(4-aminobutyl)-3-[1,6]naphthyridin-2-yl-urea hydrochloride; |
| #50 | 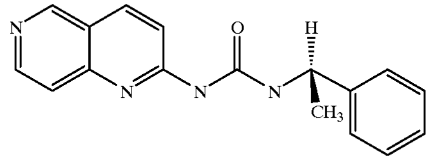 | 1-[(S)-α-methylbenzyl]-3-[1,6]naphthyridin-2-yl-urea; |
| #51 | 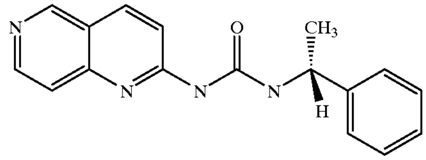 | 1-[(R)-α-methylbenzyl]-3-[1,6]naphthyridin-2-yl-urea; |
| #53 | 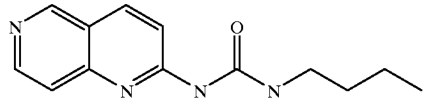 | 1-butyl-3-[1,6]naphthyridin-2-yl-urea; |
| #56 | 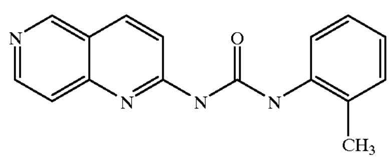 | 1-(2-methyl-phenyl)-3-[1,6]naphthyridin-2-yl-urea |
| #57 | 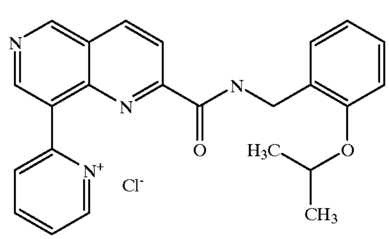 | 8-(2-pyridyl)-[1,6]naphthyridin-2-carboxylic acid (2-isopropoxybenzylamine); |
| #59 | 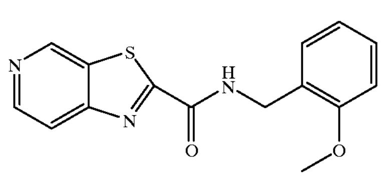 | Thiazolo[5,4-c]pyridine-2-carboxylic acid-2-methoxybenzylamide |

TABLE 1-continued

| No. | Structure | Name |
|---|---|---|
| #60 | 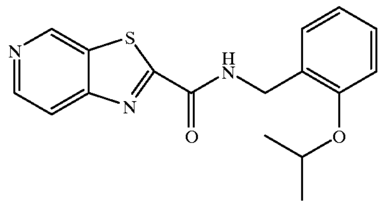 | Thiazolo[5,4-c]pyridine-2-carboxylic acid-2-isopropoxybenzylamide |
| #61 | 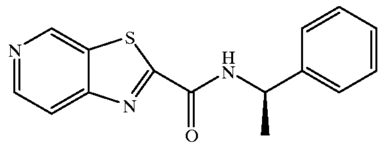 | Thiazolo[5,4-c]pyridine-2-carboxylic acid(1(R)-phenyl-ethyl)amide |
| #62 | 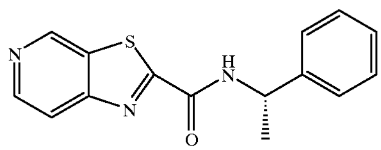 | Thiazolo[5,4-c]pyridine-2-carboxylic acid(1(S)-phenyl-ethyl)amide |
| #63 | 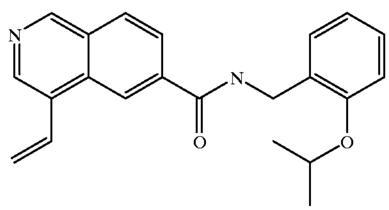 | 8-(vinyl)-[1,6]Naphthyridine-2-carboxylic acid 2-isopropoxybenzylamine |
| #64 | 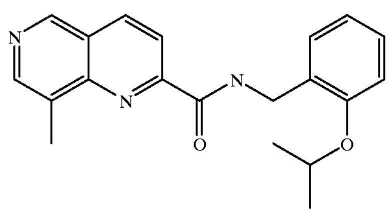 | 8-(methyl)-[1,6]Naphthyridine-2-carboxylic acid 2-isopropoxybenzylamine |
| #65 | 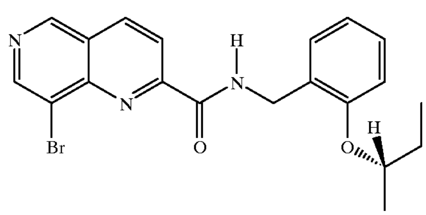 | (S)-(+)-8-Bromo-[1,6]Naphthyridine-2-Carboxylic Acid 2-Sec-Butoxy-Benzylamide |
| #66 | 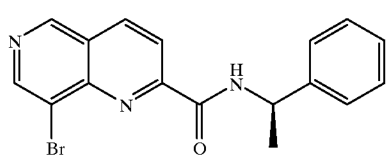 | 8-Bromo-[1,6]naphthyridine-2-carboxylic acid (1-phenyl-ethyl)-amide |
| #67 | 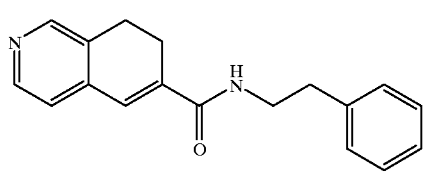 | 7,8-Dihydro-isoquinoline-6-carboxylic acid phenethyl-amide |

TABLE 1-continued

| No. | Structure | Name |
|---|---|---|
| #68 | 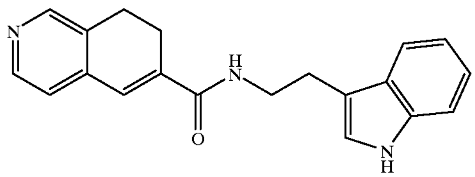 | 7,8-Dihydro-isoquinoline-6-carboxylic acid [2-(1H-indol-3-yl)-ethyl-amide |
| #69 | 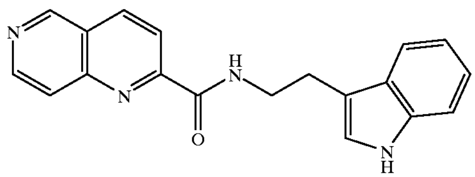 | [1,6]Naphthyridine-2-Carboxylic Acid [2-(1h-Indol-3-Yl)-Ethyl]-Amide |

More Preferred compounds of this invention include:
Compound #2 N-benzyl-2-(1,6)naphthyridinecarboxamide;
compound #4 N-(2-chlorobenzyl)-2-(1,6)naphthyridinecarboxamide;
compound #12 N-(3-methoxybenzyl)-2-(1,6)naphthyridinecarboxamide;
compound #14 N-(2,6-dimethoxybenzyl)-2-(1,6)naphthyridine-carboxamide;
compound #19 [1,6]naphthyridine-2-carboxylic acid cyclohexyl-methylamide;
compound #24 (1,6)naphthyridine-2-carboxylic acid allylamide (PFC-029);
compound #25 N-(2-methoxybenzyl)-2-(1,6)naphthyridinecarboxamide;
compound #26 N-(2propoxybenzyl)-2-[1,6]naphthyridine-2-carboxamide;
compound #28 [1,6]Naphthyridine-2-carboxylic acid (2,3,4,5-tetrahydrobenzo[B]oxepin-5-yl)-amide;
compound #31 [1,6]Naphthyridine-2-carboxylic acid 2,3-(methylenedioxy)-benzylamide;
compound #32 7,8-dihydroisoquinolin-6-carboxylic acid 2'-methoxybenzylamide;
compound #33 8-bromo-[1,6]naphthyridine-2-carboxylic acid (2-N-ethylaminobenzylamine);
compound #35 8-bromo-[1,6]naphthyridine-2-carboxylic acid (2-methoxybenzylamine)
compound #36 8-chloro-[1,6]naphthyridine-2-carboxylic acid (2-isopropoxybenzylamine);
compound #40 [1,6]Naphthyridine-2-thiocarboxylic acid-2-isopropoxybenzylamine;
compound #43 [1,6]Naphthyridine-2-thiocarboxylic acid 2-methoxy-benzylamide;
compound #46 1-(2-iso-propoxy-phenyl)-3-[1,6]naphthyridin-2-yl-urea;
compound #47 1-(2-iso-propoxybenzyl)-3-[1,6]naphthyridin-2-yl-urea;
compound #51 1-[(R)-α-methylbenzyl]-3-[1,6]naphthyridin-2-yl-urea;
Compound #59 Thiazolo[5,4-c]pyridine-2-carboxylic acid-2-methoxybenzylamide;
Compound #60 Thiazolo[5,4-c]pyridine-2-carboxylic acid-2-isopropoxybenzylamide;
Compound #61 Thiazolo[5,4-c]pyridine-2-carboxylic acid(1(R)-phenyl-ethyl)amide;
Compound #62 Thiazolo[5,4-c]pyridine-2-carboxylic acid(1(S)-phenyl-ethyl)amide;
Compound #63 8-(vinyl)-[1,6]Naphthyridine-2-carboxylic acid 2-isopropoxybenzylamine;
Compound #64 8-(methyl)-[1,6]Naphthyridine-2-carboxylic acid 2-isopropoxybenzylamine;
Compound #65 (S)-(+)-8-Bromo-[1,6]Naphthyridine-2-Carboxylic Acid 2-Sec-Butoxy-Benzylamide;
Compound #66 8-Bromo-[1,6]naphthyridine-2-carboxylic acid (1-phenyl-ethyl)-amide;
Compound #67 7,8-Dihydro-isoquinoline-6-carboxylic acid phenethyl-amide;
Compound #68 7,8-Dihydro-isoquinoline-6-carboxylic acid [2-(1H-indol-3-yl)-ethyl-amide; and
Compound #69 [1,6]Naphthyridine-2-Carboxylic Acid [2-(1h-Indol-3-Yl)-Ethyl]-Amide.
Most Preferred compounds of this invention include:
Compound #26 N-(2propoxybenzyl)-2-[1,6]naphthyridine-2-carboxamide;
Compound #32 7,8-dihydroisoquinolin-6-carboxylic acid 2'-methoxybenzylamide;
Compound #33 8-bromo-[1,6]naphthyridine-2-carboxylic acid (2-N-ethylaminobenzylamine);
Compound #36 8-chloro-[1,6]naphthyridine-2-carboxylic acid (2-isopropoxybenzylamine);
Compound #40 [1,6]Naphthyridine-2-thiocarboxylic acid-2-isopropoxybenzylamine;
Compound #43 [1,6]Naphthyridine-2-thiocarboxylic acid 2-methoxy-benzylamide;
Compound #46 1-(2-iso-propoxy-phenyl)-3-[1,6]naphthyridin-2-yl-urea;
Compound #47 1-(2-iso-propoxybenzyl)-3-[1,6]naphthyridin-2-yl-urea;
Compound #51 1-[(R)-α-methylbenzyl]-3-[1,6]naphthyridin-2-yl-urea;
Compound #59 Thiazolo[5,4-c]pyridine-2-carboxylic acid-2-methoxybenzylamide;
Compound #60 Thiazolo[5,4-c]pyridine-2-carboxylic acid-2-isopropoxybenzylamide;
Compound #61 Thiazolo[5,4-c]pyridine-2-carboxylic acid(1(R)-phenyl-ethyl)amide;
Compound #62 Thiazolo[5,4-c]pyridine-2-carboxylic acid(1(S)-phenyl-ethyl)amide;
Compound #63 8-(vinyl)-[1,6]Naphthyridine-2-carboxylic acid 2-isopropoxybenzylamine;
Compound #64 8-(methyl)-[1,6]Naphthyridine-2-carboxylic acid 2-isopropoxybenzylamine;
Compound #65 (S)-(+)-8-Bromo-[1,6]Naphthyridine-2-Carboxylic Acid 2-Sec-Butoxy-Benzylamide;
Compound #66 8-Bromo-[1,6]naphthyridine-2-carboxylic acid (1-phenyl-ethyl)-amide;
Compound #67 7,8-Dihydro-isoquinoline-6-carboxylic acid phenethyl-amide;
Compound #68 7,8-Dihydro-isoquinoline-6-carboxylic acid [2-(1H-indol-3-yl)-ethyl-amide; and
Compound #69 [1,6]Naphthyridine-2-carboxylic acid [2-(1h-indol-3-yl)-ethyl]-amide.
In a further preferred embodiment, the compounds of this invention include:
Compound #26 N-(2propoxybenzyl)-2-[1,6]naphthyridine-2-carboxamide;
Compound #32 7,8-dihydroisoquinolin-6-carboxylic acid 2'-methoxybenzylamide;
Compound #46 1-(2-iso-propoxy-phenyl)-3-[1,6]naphthyridin-2-yl-urea;

TABLE 1-continued

| No. | Structure | Name |
|---|---|---|

Compound #59 Thiazolo[5,4-c]pyridine-2-carboxylic acid-2-methoxybenzylamide
Compound #60 Thiazolo[5,4-c]pyridine-2-carboxylic acid-2-isopropoxybenzylamide
Compound #61 Thiazolo[5,4-c]pyridine-2-carboxylic acid(1(R)-phenyl-ethyl)amide
Compound #62 Thiazolo[5,4-c]pyridine-2-carboxylic acid(1(S)-phenyl-ethyl)amide
Compound #63 8-(vinyl)-[1,6]Naphthyridine-2-carboxylic acid-2-isopropoxybenzylamine
Compound #64 8-(methyl)-[1,6]Naphthyridine-2-carboxylic acid 2-isoporpoxybenzylamine
Compound #66 8-Bromo-[1,6]naphthyridine-2-carboxylic acid (1-phenyl-ethyl)-amide
Compound #67 7,8-Dihydro-isoquinoline-6-carboxylic acid phenethyl-amide; and
Compound #68 7,8-Dihydro-isoquinoline-6-carboxylic acid [2-(1H-indol-3-yl)-ethyl-amide Compounds of the present invention can be synthesized using conventional preparative steps and recovery methods known to those skilled in the art of organic chemistry. A preferred synthetic route for producing compounds of formula (VI) when A is O, involves coupling a carboxylic acid intermediate of formula a with an amino intermediate of formula b of scheme 1. The reaction will be under suitable conditions for amide bond formation i.e. in the presence of a suitable coupling agent such as EDC or dCC, to yield final compound of formula (VI). The reaction is illustrated in scheme 1. Compounds of formula (VI) with A as O can be converted to compounds of formula (VI) with A as S by reacting them with thionation agents such as Lawesson's reagent. The use of Lawesson's reagent is well known in the art (for example, see *Synthesis,* 941 (1979); *Tetrahedron,* 35, 2433 (1979); and *Tet. Lett.,* 21, 4061 (1980).

A preferred synthetic route for producing bicyclic compounds of formula (VII) involved coupling a bicyclic amino intermediate of formula c with an amido moiety d. This reaction is illustrated by scheme 2. The reaction will be under suitable condition for <<urea>> bond formation, in appropriate solvent to yield to compounds of formula (VII). Introduction of an $R_2$ substituent on the nitrogen can be done using methods known in the art. The urea bond of compounds (VII) can also be converted to a thiourea by reacting the compounds with thionation agents as mentioned above.

SCHEME 1

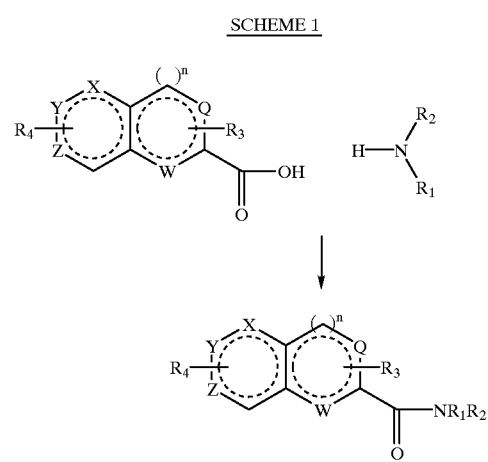

wherein X, Y, Z, $R_1$ to $R_4$ and n are as previously defined.

Intermediates a, b and c may be obtained from commercial sources, for instance, 2-carboxy-[1,6]naphthyridine (Peakdale Fine Chemicals, Glossop, Derbyshire UK, PFC-027); 6,7-dibromo-4-hydroxy-[1,5]naphthyridine-2-carboxylic acid (Pomorski et al Rocz. Chem., 1974, 48(2): 321); 1,2,3,4-tetrahydro-8-hydroxy-[1,6]naphthyridine-2-carboxylic acid (Abe et al Tet. Lett., 1977, 9:735). Or, alternatively intermediates a ,b and c may be prepared according to established synthetic techniques.

Scheme 2

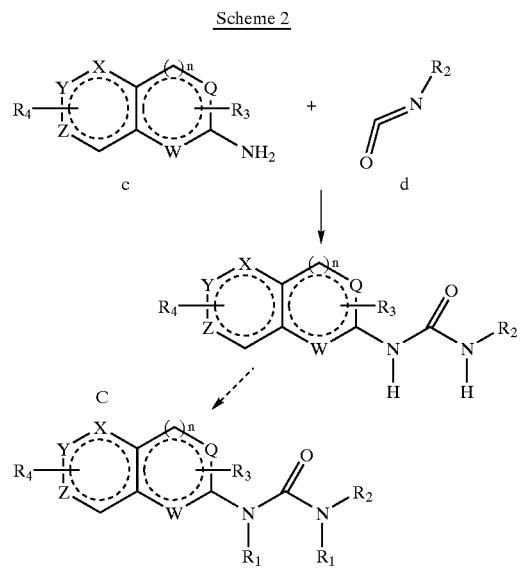

Compounds according to formula (VIII) thiazolo[5,4-c] pyridines, may be synthesized using established organic chemistry techniques. For example, a synthetic scheme is described in Katner et al (1990) J. Heterocycl. Chem. 27(3):563.

It will be appreciated that certain substituents require protection during the course of the synthesis and subsequent deprotection. For example, when $R_3$ or $R_4$ is hydroxyl, it may be necessary to protect it by converion to an alkoxy or an ester and subsequently deprotected. Protective groups for other substituents are described in *Protective Groups in Organic Synthesis,* 2nd ed., Greene and Wuts, John Wiley & Sons, New York, 1991.

It will be appreciated by those skilled in the art that the compounds of formula I, depending on the substituents, may contain one or more chiral centers and thus exist in the form of many different isomers, optical isomers (i.e. enantiomers) and mixtures thereof including racemic mixtures. All such isomers, enantiomers and mixtures thereof including racemic mixtures are included within the scope of the invention.

According to methods of the present invention, compounds of formula (I) are administered to a mammal to inhibit replication of or reduce cytopathic effects of viruses. In particular the HIV virus which is known to be the causative agent in Acquired Immune Deficiency Syndrome (AIDS). Other viruses inhibited with compounds of formula (I) include but are not limited to HSV-1 (herpes simplex virus type 1), HSV-2 (herpes simplex virus type 2), HBV (hepatitis B virus), HCV (hepatitis C virus), HPV (human papilloma virus), influenza A, Influenza B, RSV (respiratory syncitial virus), RV (rhinovirus), AV (adenovirus), Parainfluenza virus and cytomegalovirus (CMV).

In a preferred embodiment compounds of formula (I) are administered to a mammal to inhibit replication of or reduce cytopathic effects of HIV virus In a preferred embodiment compounds of formula (I) are administered to a mammal to inhibit replication of or reduce cytopathic effects of hepatitis B virus.

In a preferred embodiment compounds of formula (I) are administered to a mammal to inhibit replication of or reduce cytopathic effects of hepatitis C virus In a preferred embodiment compounds of formula (I) are administered to a mammal to inhibit replication of or reduce cytopathic effects of HSV-1 (herpes simplex virus type 1) or HSV-2 (herpes simplex virus type 2).

In a preferred embodiment compounds of formula (I) are administered to a mammal to inhibit replication of or reduce cytopathic effects of influenza A.

In a preferred embodiment compounds of formula (I) are administered to a mammal to inhibit replication of or reduce cytopathic effects of Influenza B.

In a preferred embodiment compounds of formula (I) are administered to a mammal to inhibit replication of or reduce cytopathic effects of RSV (respiratory syncitial virus).

In a preferred embodiment compounds of formula (I) are administered to a mammal to inhibit replication of or reduce cytopathic effects of RV (rhinovirus).

In a preferred embodiment compounds of formula (I) are administered to a mammal to inhibit replication of or reduce cytopathic effects of AV (adenovirus).

In a preferred embodiment compounds of formula (I) are administered to a mammal to inhibit replication of or reduce cytopathic effects of parainfluenza virus.

Furthermore, compounds of formula (I) interact with the nuclear factor κ B (NFκB) signal transduction pathway. Consequently compounds of formula (I) may be used to treat conditions mediated by tumour necrosis factor (TNFα) or other cytokines under transcriptional control of NFκB. Conditions include acute and chronic inflammatory diseases such as rheumatoid arthritis, osteoarthritis, Krohn's disease, colitis, and septic shock.

Additionally, effective dose of compounds of formula (I) and pharmaceutically acceptable salts, capable of inhibiting viral replication, may be used in combination with a second antiviral agent selected form the group consisting of Lamivudine, hydroxymethyl-4-(cytosin-1'-yl)-1,3-oxathiolane, FTC, AZT, d4T, nevirapine, DMP-226, nelfinavir, indinavir, delavirdine, 9-[(2-hydroxymethyl)-1,3-dioxolan-4-yl]guanine, 2-amino-9-[(2-hydroxymethyl)-1,3-dioxolan-4-yl]adenine, MKC-442, 1592U89 (abacavir), 141W94, MK-639, Indinavir, saquinavir, ritonavir, TIBO, HEPT, BHAP,, α-APA, TSAO, calanolides, L-697,661, 2',3'-dideoxycytidine (ddC), 2',3'-dideoxyadenosine, 2',3'-dideoxyinosine (ddI), 3'-deoxythymidine, 2',3'-dideoxy-2', 3'-didehydro-thymidine, and 2',3'-dideoxy-2',3'-didehydrocytidine and ribavirin; acyclic nucleosides such as acyclovir, ganciclovir, interferons such as alpha-, beta-and gamma-interferon; glucuronation inhibitors such as probenecid; nucleoside transport inhibitors such as dipyridamole; immunomodulators such as interleukin II (IL2) and granulocyte macrophage colony stimulating factor (GM-CSF), erythropoietin, ampligen, thymomodulin, thymopentin, foscarnet, glycosylation inhibitors such as 2-deoxy-D-glucose, castanospermine, 1-deoxynojirimycin; and inhibitors of HIV binding to CD4 receptors such as soluble CD4, CD4 fragments, CD4-hybrid molecules and inhibitors of the HIV aspartyl protease such as L-735,524.

The present invention also provides antiviral compositions which comprise a pharmaceutically acceptable carrier or adjuvant and an amount of a compound of formula (I), effective to inhibit viral replication in a mammal. The proportion of each carrier, diluent or adjuvant is determined by the solubility and chemical nature of the compound and the route of administration according to standard pharmaceutical practice.

Viral replication inhibiting compositions include those suitable for oral, rectal, nasal, topical (including buccal and sub-lingual), vaginal or parenteral (including intramuscular, sub-cutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Therapeutic and prophylactic methods of this invention comprise the step of treating patients in a pharmaceutically acceptable manner with those compounds or compositions. Such compositions may be in the form of tablets, capsules, caplets, powders, granules, lozenges, suppositories, reconstitutable powders, or liquid preparations, such as oral or sterile parenteral solutions or suspensions.

Compounds of formula (VIII) wherein A is O may also be administered via an intraocular implant for treating retinitis as a result of CMV infection. In particular, these compounds may be embedded in a polymer based implant which will be release into the eye over an extended period of time.

In order to obtain consistency of administration, it is preferred that a composition of the invention is in the form of a unit dose. The unit dose presentation forms for oral administration may be tablets and capsules and may contain conventional excipients. For example, binding agents, such as acacia, gelatin, sorbitol, or polyvinylpyrrolidone; fillers, such as lactose, sugar, maize-starch, calcium phosphate, sorbitol or glycine; tableting lubricants such as magnesium stearate; disintegrants, such as starch, polyvinylpyrrolidone, sodium starch glycollate or microcrystalline cellulose; or pharmaceutically acceptable wetting agents such as sodium lauryl sulphate.

The compounds may be injected parenterally; this being intramuscularly, intravenously, or subcutaneously. For parenteral administration, the compound may be used in the form of sterile solutions containing other solutes, for example, sufficient saline or glucose to make the solution isotonic. The amount of active ingredient administered parenterally will be approximately 0.01 to 250 mg/kg/day, preferably about 1 to 10 mg/kg/day, more preferably about 0.5 to 30 mg/kg/day, and more most preferably about 1–20 mg/kg/day.

The compounds may be administered orally in the form of tablets, capsules, or granules containing suitable excipients such as starch, lactose, white sugar and the like. The compounds may be administered orally in the form of solutions which may contain coloring and/or flavoring agents. The compounds may also be administered sublingually in the form of tracheas or lozenges in which each active ingredient is mixed with sugar or corn syrups, flavoring agents and dyes, and then dehydrated sufficiently to make the mixture suitable for pressing into solid form. The amount of active ingredient administered orally will depend on bioavailability of the specific compound.

The solid oral compositions may be prepared by conventional methods of blending, filling, tableting, or the like.

Repeated blending operations may be used to distribute the active agent throughout those compositions employing large quantities of fillers. Such operations are, of course, conventional in the art. The tablets may be coated according to methods well known in normal pharmaceutical practice, in particular with an enteric coating.

Oral liquid preparations may be in the form of emulsions, syrups, or elixirs, or may be presented as a dry product for reconstitution with water or other suitable vehicle before use. Such liquid preparations may or may not contain conventional additives. For example suspending agents, such as sorbitol, syrup, methyl cellulose, gelatin, hydroxyethylcellulose, carboxymethylcellulose, aluminum stearate gel, or hydrogenated edible fats; emulsifying agents, such as sorbitan monooleate or acaci; non-aqueous vehicles (which may include edible oils), such as almond oil, fractionated coconut oil, oily esters selected from the group consisting of glycerine, propylene glycol, ethylene glycol, and ethyl alcohol; preservatives, for instance methyl para-hydroxybenzoate, ethyl para-hydroxybenzoate, n-propyl parahydroxybenzoate, or n-butyl parahydroxybenzoate of sorbic acid; and, if desired, conventional flavoring or coloring agents.

For parenteral administration, fluid unit dosage forms may be prepared by utilizing the peptide and a sterile vehicle, and, depending on the concentration employed, may be either suspended or dissolved in the vehicle. Once in solution, the compound may be injected and filter sterilized before filling a suitable vial or ampoule and subsequently sealing the carrier or storage package. Adjuvants, such as a local anesthetic, a preservative or a buffering agent, may be dissolved in the vehicle prior to use. Stability of the pharmaceutical composition may be enhanced by freezing the composition after filling the vial and removing the water under vacuum, (e.g., freeze drying the composition). Parenteral suspensions may be prepared in substantially the same manner, except that the peptide should be suspended in the vehicle rather than being dissolved, and, further, sterilization is not achievable by filtration. The compound may be sterilized, however, by exposing it to ethylene oxide before suspending it in the sterile vehicle. A surfactant or wetting solution may be advantageously included in the composition to facilitate uniform distribution of the compound.

For topical administration to the epidermis, the compounds according to the present invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

The pharmaceutical compositions of this invention comprise a viral replication inhibiting amount of a compounds of formula (I) and a pharmaceutically acceptable carrier, diluent or adjuvant. Typically, they contain from about 0.1% to about 99% by weight of active compound, and preferably from about 10% to about 60% by weight depending on which method of administration is employed.

A viral replication inhibiting amount is that amount of active compound required to slow the progression of viral replication or reduce viral load from that which would otherwise occur without administration of said compound. Or, it is an amount of active compound required to slow the progression or reduce the intensity of symptoms resulting from viral infection or elimination thereof.

Viral inhibiting activity of compounds of the invention can be determined according to the plaque reduction assay for CMV or other standard assays for other viruses which are described in detail in the examples. Under these particular conditions, a compound having anti-CMV activity will exhibit an $IC_{50}$ of approximately 50 μg/ml or less, preferably 25 μg/ml or less, more preferably 10 μg/ml or less, and most preferably less than 1 μg/ml.

Physicians will determine the dosage of the present therapeutic agents which will be most suitable. Dosages may vary with the mode of administration and the particular compound chosen. In addition, the dosage may vary with the particular patient under treatment. The dosage of the compound used in the treatment will vary, depending on viral load, the weight of the patient, the relative efficacy of the compound and the judgment of the treating physician. Such therapy may extend for several weeks or months, in an intermittent or uninterrupted manner.

To further assist in understanding the present invention, the following non-limiting examples are provided.

EXAMPLE 1

Synthesis

Compound #1

N-(2-methylbenzyl)-2-[1,6]naphthyridine-carboxamide

To a stirring mixture of 2-[1,6]naphthyridinecarboxylic acid (50 mg, 0.287 mmol), in anhydrous THF (5 ml) at 0° C. was added triethylamine (44 ml, 0.316 mmol). After 5 min, isopropylchloroformate (0.316 ml, 1 M solution in toluene, 0.316 mmol) was added. The mixture was stirred at 0° C. for 20 min. then 2-methylbenzylamine (53.46 ml, 0.43 mmol) was added to the mixture at 0° C. The resulting mixture was allowed to warm to room temperature and stirred at room temperature for 5 h then diluted in $CH_2Cl_2$ (100 ml). The organic layer was washed with water, dried over anhydrous $MgSO_4$, and concentrated to give the crude mixture. Chromatography of the crude (Hex:EtOAc=1:1 to pure EtOAc) afforded desired product as white solid (29.8 mg, 37%): m.p. 120–121° C.

Compound #2

N-benzyl-2-[1,6]naphthyridinecarboxamide

To a stirring mixture of 2-[1,6]naphthyridinecarboxylic acid (50 mg, 0.287 mmol), 1-hydroxybenzo-triazole hydrate (42.7 mg, 0.316 mmol), benzylamine (45 mg, 0.42 mmol) in anhydrous THF (5 ml) at 0° C. was added 1-(3-dimethylaminopropyl)-3-ethylcarbodiimide hydrochloride (60.6 mg, 0.316 mmol). The resulting mixture was allowed to stir at RT. After 20 min, DMF (2ml) was added to the reaction mixture and the mixture was allowed to stir at room temperature overnight and it was found to be clear. The solvent was removed under vacuum and the resulting residue was redissolved in $CH_2Cl_2$ (100 ml). The organic layer was washed with aqueous $NaHCO_3$, dried over anhydrous $MgSO_4$, and concentrated to give the crude mixture. Chromatography of the crude (Hex:EtOAc=1:1 to pure EtOAc) afforded desired product as white solid (97 mg, 99%): m.p.113–115° C.

Compound #3

N-(2-bromobenzyl)-2-[1,6]naphthyridine-carboxamide

To a stirring solution of 4-bromobenzylamine hydrochloride (97.8 mg, 98%, 0.431 mmol) in anhydrous DMF (5 ml) was added triethylamine (60.1 ul. 0.431 mmol), After 5 min, 2-[1,6]naphthyridinecarboxylic acid (50 mg, 0.287 mmol), 1-hydroxybenzotriazole hydrate (42.7 mg, 0.316 mmol) and 1-(3-dimethylamino-propyl)-3-ethylcarbodiimide hydrochloride (60.6 mg, 0.316 mmol) was sequentially added. The resulting mixture was allowed to stir at room temperature for overnight and it was found to be clear. The solvent was removed under vacuum and the resulting residue was redissolved in $CH_2Cl_2$ (100 ml). The resulting mixture was allowed to stir at room temperature overnight and it was found to be clear. The solvent was removed under vacuum and the resulting residue was redissolved in $CH_2Cl_2$ (100 ml). The organic layer was washed with aqueous $NaHCO_3$, dried over anhydrous $MgSO_4$, and concentrated to give the crude mixture. Chromatography of the crude (Hex:EtOAc= 1:1 to pure EtOAc) afforded desired product as white solid (97 mg, 99%): m.p. 149–150° C.

Compound #4

N-(2-chlorobenzyl)-2-[1,6]naphthyridine-carboxamide

To a stirring mixture of 2-[1,6]naphthyridinecarboxylic acid (50 mg, 0.287 mmol) in anhydrous DMF (5 ml) at room temperature was sequentially added 1-hydroxybenzotriazole hydrate (42.7 mg, 0.316 mmol), 2-chlorobenzylamine (54.7 µl, 95%, 0.43 mmol) and 1-(3-dimethylaminopropyl)-3-ethylcarbodiimide hydrochloride (60.6 mg, 0.316 mmol). The resulting mixture was allowed to stir at room temperature overnight and it was found to be clear. The solvent was removed under vacuum and the resulting residue was redissolved in $CH_2Cl_2$ (100 ml). The resulting mixture was allowed to stir at room temperature overnight and it was found to be clear. The solvent was removed under vacuum and the resulting residue was redissolved in $CH_2Cl_2$ (100 ml). The organic layer was washed with aqueous $NaHCO_3$, dried over anhydrous $MgSO_4$, and concentrated to give the crude mixture. Chromatography of the crude (Hex:EtOAc= 1:1 to pure EtOAc) afforded desired product as white solid (83 mg, 97%): m.p. 120–121° C.

Compound #5

N-(2-bromobenzyl)-2-[1,6]naphthyridine-carboxamide

To a stirring solution of 2-bromobenzylamine hydrochloride (80.7 mg, 95%, 0.345 mmol) in anhydrous DMF (5 ml) was added triethylamine (51.8 ul. 0.345 mmol), After 5 min, 2-[1,6]naphthyridinecarboxylic acid (40 mg, 0.229 mmol), 1-hydroxybenzotriazole hydrate (34.2 mg, 0.253 mmol) and 1-(3-dimethylamino-propyl)-3-ethylcarbodiimide hydrochloride (48.5 mg, 0.253 mmol) was sequentially added. The resulting mixture was allowed to stir at room temperature for 4 h and it was found to be clear. The solvent was removed under vacuum and the resulting residue was redissolved in $CH_2Cl_2$ (100 ml). The organic layer was washed with aqueous $NaHCO_3$, dried over anhydrous $MgSO_4$, and concentrated to give the crude mixture. Chromatography of the crude (Hex:EtOAc=1:1 to pure EtOAc) afforded desired product as white solid (70 mg, 89%): m.p. 129–130° C.

Compound #6

N-(3-bromobenzyl)-2-[1,6]naphthyridine-carboxamide

To a stirring solution of 3-bromobenzylamine hydrochloride (77.5 mg, 0.345 mmol) in anhydrous DMF (5 ml) was added triethylamine (51.8 ul. 0.345 mmol), After 5 min, 2-[1,6]naphthyridinecarboxylic acid (40 mg, 0.229 mmol), 1-hydroxybenzotriazole hydrate (34.2 mg, 0.253 mmol) and 1-(3-dimethylamino-propyl)-3-ethylcarbodiimide hydrochloride (48.5 mg, 0.253 mmol) was sequentially added. The resulting mixture was allowed to stir at room temperature overnight and it was found to be clear. The solvent was removed under vacuum and the resulting residue was redissolved in $CH_2Cl_2$ (100 ml). The organic layer was washed with aqueous $NaHCO_3$, dried over anhydrous $MgSO_4$, and concentrated to give the crude mixture. Chromatography of the crude (Hex:EtOAc=1:1 to pure EtOAc) afforded desired product as white solid (64 mg, 81%): m.p. 112–113° C.

Compound #7

N-(2-fluorobenzyl)-2-[1,6]naphthyridine-carboxamide

To a stirring mixture of 2-[1,6]naphthyridinecarboxylic acid (50 mg, 0.287 mmol) in anhydrous DMF (6.3 mL) at room temperature was added sequentially 1-hydroxybenzotriazole hydrate (42.7 mg, 0.316 mmol), 2-fluorobenzyl amine (51.0 µL, 0.431 mmol) and 1-(3-dimethylaminopropyl)-3-ethylcarboiimide hydrochloride (61.8 mg, 0.316 mmol). The resulting mixture was allowed to stir at room temperature overnight and it was found to be clear. The solvent was removed under vacuum and the resulting residue was re-dissolved in $CH_2Cl_2$ (50 mL). The organic layer was washed with aqueous $NaHCO_3$, dried over anhydrous $Na_2SO_4$, and concentrated to give the crude mixture. Flash column chromatography of the crude (50% hexane/ethyl acetate to 100% ethyl acetate) afforded the desired product as a white solid (79.2 mg, 98%): m.p. 110–111° C.

Compound #8

N-(4-chlorobenzyl)-2-[1,6]naphthyridine-carboxamide

To a stirring mixture of 2-[1,6]naphthyridinecarboxylic acid (50 mg, 0.287 mmol) in anhydrous DMF (6.3 mL) at room temperature was added sequentially-hydroxybenzotriazole hydrate (42.7 mg, 0.316 mmol), 4-chlorobenzyl amine (53.5 µL, 0.431 mmol) and 1-(3-dimethylaminopropyl)-3-ethylcarboiimide hydrochloride (61.8 mg, 0.316 mmol). The resulting mixture was allowed to stir at room temperature overnight and it was found to be clear. The solvent was removed under vacuum and the resulting residue was re-dissolved in $CH_2Cl_2$ (50 mL). The organic layer was washed with aqueous $NaHCO_3$, dried over anhydrous $Na_2SO_4$, and concentrated to give the crude mixture. Flash column chromatography of the crude (50% hexane/ethyl acetate to 100% ethyl acetate) afforded the desired product as a white solid (80.3 mg, 94%): m.p. 110–111 ° C.

Compound #9

N-(2-ethoxybenzyl)-2-[1,6]naphthyridine-carboxamide

To a stirring mixture of 2-[1,6]naphthyridinecarboxylic acid (50 mg, 0.287 mmol) in anhydrous DMF (6.3 mL) at room temperature was added sequentially 1-hydroxybenzotriazole hydrate (42.7 mg, 0.316 mmol), 2-ethoxybenzyl amine (64.9 µL, 0.431 mmol) and 1-(3-dimethylaminopropyl)-3-ethylcarboiimide hydrochloride (61.8 mg, 0.316 mmol). The resulting mixture was allowed to stir at room temperature overnight and it was found to be clear. The solvent was removed under vacuum and the resulting residue was re-dissolved in $CH_2Cl_2$ (50 mL). The organic layer was washed with aqueous $NaHCO_3$, dried over anhydrous $Na_2SO_4$, and concentrated to give the crude mixture. Flash column chromatography of the crude (50% hexane/ethyl acetate to 100% ethyl acetate) afforded the desired product as a white solid (85.0 mg, 96%): m.p. 79–80 ° C.

Compound #10

[1,6]naphthyridine-2-carboxylic acid indan-1-ylamide

To a stirring mixture of 2-[1,6]naphthyridinecarboxylic acid (50 mg, 0.287 mmol) in anhydrous DMF (6.3 mL) at room temperature was added sequentially 1-hydroxybenzotriazole hydrate (42.7 mg, 0.316 mmol), 1-aminoindan (56.0 µL, 0.431 mmol) and 1-(3-dimethylaminopropyl)-3-ethylcarboiimide hydrochloride (61.8 mg, 0.316 mmol). The resulting mixture was allowed to stir at room temperature overnight and it was found to be clear. The solvent was removed under vacuum and the resulting residue was re-dissolved in $CH_2Cl_2$ (50 mL). The organic layer was washed with aqueous $NaHCO_3$, dried over anhydrous $Na_2SO_4$, and concentrated to give the crude mixture. Flash column chromatography of the crude (50% hexane/ethyl acetate to 100% ethyl acetate) afforded the desired product as a white solid (80.1 mg, 96%): m.p. 156–157° C.

Compound #11
[1,6]naphthyridine-2-carboxylic acid (1,2,3,4-tetrahydro-naphthalen-1-yl)-amide To a stirring mixture of 2-[1,6]naphthyridinecarboxylic acid (50 mg, 0.287 mmol) in anhydrous DMF (6.3 mL) at room temperature was added sequentially 1-hydroxybenzotriazole hydrate (42.7 mg, 0.316 mmol), 1,2,3,4-tetrahydro-1-naphthylamine (63.0 µL, 0.431 mmol) and 1-(3-dimethylaminopropyl)-3-ethylcarboiimide hydrochloride (61.8 mg, 0.316 mmol). The resulting mixture was allowed to stir at room temperature overnight and it was found to be clear. The solvent was removed under vacuum and the resulting residue was re-dissolved in $CH_2Cl_2$ (50 mL). The organic layer was washed with aqueous $NaHCO_3$, dried over anhydrous $Na_2SO_4$, and concentrated to give the crude mixture. Flash column chromatography of the crude (50% hexane/ethyl acetate to 100% ethyl acetate) afforded the desired product as a white solid (87.0 mg, 100%): m.p. 164–165° C.

Compound #12
N-(3-methoxybenzyl)-2-[1,6]naphthyridine-carboxamide

To a stirring mixture of 2-[1,6]naphthyridinecarboxylic acid (50 mg, 0.287 mmol) in anhydrous DMF (1.0 mL) at room temperature was added sequentially 1-hydroxybenzotriazole hydrate (42.7 mg, 0.316 mmol), 3-methoxybenzylamine (56.6 µL, 0.431 mmol) and 1-(3-dimethylaminopropyl)-3-ethylcarboiimide hydrochloride (61.8 mg, 0.316 mmol). The resulting mixture was allowed to stir at room temperature overnight and it was found to be clear. The solvent was removed under vacuum. Flash column chromatography of the residue (50% hexane/ethyl acetate to 100% ethyl acetate) afforded the desired product as a clear oil (79.1 mg, 94%).

Compound #13
N-(2-trifluoromethylbenzyl)-2-[1,6]naphthyridinecarboxamide

To a stirring mixture of 2-[1,6]naphthyridinecarboxylic acid (50 mg, 0.287 mmol) in anhydrous DMF (1.0 mL) at room temperature was added sequentially 1-hydroxybenzotriazole hydrate (42.7 mg, 0.316 mmol), 2-(trifluoromethyl)-benzylamine (61.6 µL, 0.431 mmol) and 1-(3-dimethylaminopropyl)-3-ethylcarboiimide hydrochloride (61.8 mg, 0.316 mmol). The resulting mixture was allowed to stir at room temperature overnight and it was found to be clear. The solvent was removed under vacuum. Flash column chromatography of the residue (50% hexane/ethyl acetate to 100% ethyl acetate) afforded the desired product as a white solid (90.9 mg, 96%): m.p. 125–127° C.

Compound #14
N-(2,6-dimethoxybenzyl)-2-[1,6]naphthyridine-carboxamide

To a stirring mixture of 2-[1,6]naphthyridinecarboxylic acid (50 mg, 0.287 mmol) in anhydrous DMF (1.0 mL) at room temperature was added sequentially 1-hydroxybenzotriazole hydrate (42.7 mg, 0.316 mmol), 2,6-dimethoxybenzylamine (75.0 mg, 0.431 mmol) and 1-(3-dimethylaminopropyl)-3-ethylcarboiimide hydrochloride (61.8 mg, 0.316 mmol). The resulting mixture was allowed to stir at room temperature overnight and it was found to be clear. The solvent was removed under vacuum. Flash column chromatography of the residue (50% hexane/ethyl acetate to 100% ethyl acetate) afforded the desired product as a white solid (90.6 mg, 98%): m.p. 169–171° C.

Compound #15
[1,6]naphthyridine-2-carboxylic acid (trans-2-phenyl-cyclopropyl)-amide To a stirring mixture of trans-2-phenylcyclopropylamine hydrochloride (75.3 mg, 0.431) in anhydrous DMF (1.0 mL) was added triethylamine (60.0 µL, 0.431 mmol). After 5 minutes, 2-[1,6]naphthyridinecarboxylic acid (50 mg, 0.287 mmol), 1-hydroxybenzotriazole hydrate (42.7 mg, 0.316 mmol), and 1-(3-dimethylaminopropyl)-3-ethylcarboiimide hydrochloride (61.8 mg, 0.316 mmol) were added sequentially. The resulting mixture was allowed to stir at room temperature overnight and it was found to be clear. The solvent was removed under vacuum. Flash column chromatography of the residue (50% hexane/ethyl acetate to 100% ethyl acetate) afforded the desired product as a white solid (79.2 mg, 95%): m.p. 123–124 ° C.

Compound #16
N-(2-amino-6-fluorobenzyl)-2-[1,6]naphthyridinecarboxamide

To a stirring mixture of 2-[1,6]naphthyridinecarboxylic acid (50 mg, 0.287 mmol) in anhydrous DMF (1.0 mL) at room temperature was added sequentially 1-hydroxybenzotriazole hydrate (42.7 mg, 0.316 mmol), 2-amino-6-fluorobenzylamine (60.0 µL) and 1-(3-dimethylaminopropyl)-3-ethylcarboiimide hydrochloride (61.8 mg, 0.316 mmol). The resulting mixture was allowed to stir at room temperature overnight and it was found to be clear. The solvent was removed under vacuum. 1Flash column chromatography of the residue (50% hexane/ethyl acetate to 100% ethyl acetate) afforded the desired product as a white solid (80.0 mg, 94%): m.p. 165 (dec.).

Compound #17
[1,6]naphthyridine-2-carboxylic acid (1-phenylethyl) amide

To a stirring mixture of 2-[1,6]naphthyridinecarboxylic acid (50 mg, 0.287 mmol) in anhydrous DMF (1.0 mL) at room temperature was added sequentially 1-hydroxybenzotriazole hydrate (42.7 mg, 0.316 mmol), 1-phenylethylamine (56.1 µL, 0.431 mmol) and 1-(3-dimethylaminopropyl)-3-ethylcarboiimide hydrochloride (61.8 mg, 0.316 mmol). The resulting mixture was allowed to stir at room temperature overnight and it was found to be clear. The solvent was removed under vacuum. Flash column chromatography of the residue (50% hexane/ethyl acetate to 100% ethyl acetate) afforded the desired product as a clear oil (78.7 mg, 99%).

Compound #18
[1,6]naphthyridine-2-carboxylic acid (pyridine-2-ylmethyl) amide

To a stirring mixture of 2-[1,6]naphthyridinecarboxylic acid (50 mg, 0.287 mmol) in anhydrous DMF (1.0 mL) at room temperature was added sequentially 1-hydroxybenzotriazole hydrate (42.7 mg, 0.316 mmol), 2-(aminomethyl)pyridine (45.3 µL, 0.431 mmol) and 1-(3-dimethylaminopropyl)-3-ethylcarboiimide hydrochloride (61.8 mg, 0.316 mmol). The resulting mixture was allowed to stir at room temperature overnight and it was found to be clear. The solvent was removed under vacuum. Flash column chromatography of the residue (50% hexane/ethyl acetate to 5% methanol/ethyl acetate) afforded the desired product as a light brown solid (78.7 mg, 99%): m.p. 123–125° C.

Compound #19
[1,6]naphthyridine-2-carboxylic acid cyclohexyl-methylamide

To a stirring mixture of 2-[1,6]naphthyridinecarboxylic acid (50 mg, 0.287 mmol) in anhydrous DMF (1.0 mL) at room temperature was added sequentially 1-hydroxybenzotriazole hydrate (42.7 mg, 0.316 mmol), cyclohexanemethylamine (57.2 µL, 0.431 mmol) and 1-(3-dimethylaminopropyl)-3-ethylcarboiimide hydrochloride (61.8 mg, 0.316 mmol). The resulting mixture was allowed to stir at room temperature overnight and it was found to be clear. The solvent was removed under vacuum. Flash column chromatography of the residue (100% ethyl acetate) afforded the desired product as a white solid (74.9 mg, 97%): m.p. 62–63° C.

Compound #20

(3,4-dihydro-1h-isoquinolin-2-yl)-[1,6]naphthyridin-2-yl-methanone

To a stirring mixture of 2-[1,6]naphthyridinecarboxylic acid (50 mg, 0.287 mmol) in anhydrous DMF (1.0 mL) at room temperature was added sequentially 1-hydroxybenzotriazole hydrate (42.7 mg, 0.316 mmol), 1,2,3,4-tetrahydroisoquinoline (55.6 µL, 0.431 mmol) and 1-(3-dimethylaminopropyl)-3-ethylcarboiimide hydrochloride (61.8 mg, 0.316 mmol). The resulting mixture was allowed to stir at room temperature overnight and it was found to be clear. The solvent was removed under vacuum. Flash column chromatography of the residue (100% ethyl acetate) afforded the desired product as a white solid (79.1 mg, 95%): m.p. 98–100° C.

Compound #21

N-(2-methylthiobenzyl)-2-[1,6]naphthyridine carboxamide

To a stirring mixture of 2-methylsulfanylbenzylamine hydrochloride (81.7 mg, 0.431) in anhydrous DMF (1.0 mL) was added triethylamine (60.0 µL, 0.431 mmol). After 5 minutes, 2-[1,6]naphthyridinecarboxylic acid (50 mg, 0.287 mmol), 1-hydroxybenzotriazole hydrate (42.7 mg, 0.316 mmol), and 1-(3-dimethylaminopropyl)-3-ethylcarboiimide hydrochloride (61.8 mg, 0.316 mmol) were added sequentially. The resulting mixture was allowed to stir at room temperature overnight. The solvent was removed under vacuum. Flash column chromatography of the residue (50% hexane/ethyl acetate to 100% ethyl acetate) afforded the desired product as a light brown solid (88.2 mg, 99%): m.p. 102–103° C.

Compound #32

7,8-dihydroisoquinolin-6-carboxylic acid 2-methoxybenzylamide step 1

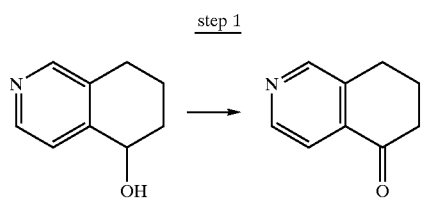

Chromium trioxide (15.50, 173.1o mmol) was added in one protion to a solution of pyridine (28 mL, 346.20 mmol) in dichloromethane (175 mL) at 0° C. The cooling bath was removed and the mixture was allowed to stir for 30 min. To that solution was then added a solution of the alcohol (Cheng, C. Y.;Hsin, L. W.;Liou, J. P. *Tetrahedron*, 1996, 52, 10935). (3.851 g, 25.85 mmol) in dichloromethane (15 mL). The mixture was then stirred at room temperature for 2 h and the solution was decanted, the solvent was then removed and the residue was purified by chromatography eluting with 2% MeOH in $CH_2Cl_2$. The desired compound was obtained as a pale yellow solid (2.662 g, 70%)

$^1$H NMR (400 MHz,$CDCl_3$) δ: 8.69 (s, 1 H, H-1), 8.64 (d, 1 H, H-2, J=7.1 Hz), 7.78 (d, 1 H, H-4, J=7.1 Hz), 2.99 (t, 2 H, H-6, J=6.2 Hz), 2.73 (t, 2 H, H-8, J=6.3 Hz), 2.21 (t, 2 H, H-7, J=6.2 Hz).

Step 2

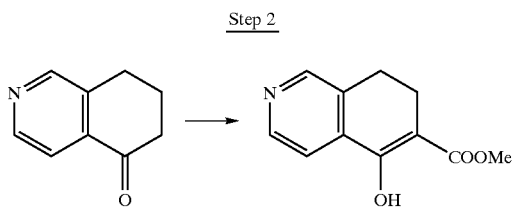

LiHMDS in THF (1 M, 11.0 mL, 1 mmol) was added to a solution name (Lithrium 1,1,1,3,3,3-hexamethyidisilazane) of ketone (115 mg, 0.78 mmol) in THF (3 mL) at-78° C. After 15 min at this temperature methyl cyanoformate (0.3 mL, 3.9 mmol) was added and the mixture was allowed stir overnight. The reaction was then quenched with saturated ammonium chloride and extracted with ethyl acetate. After drying ($Na_2SO_4$). The residue was triturated with cold ethyl acetate yielding the desired compound. (75 mg, 47%)

$^1$H NMR (400 MHz,$CDCl_3$) δ: 11.81 (s, 1 H, OH), 8.63 (d, 1 H, H-3, J=5.9 Hz),), 8.58 (s, 1 H, H-1), 8.16 (d, 1 H, H-4, J=5.9 Hz), 3.93 (s, 3 H, $OCH_3$), 3.05 (t, 2 H, H-8, J=7.8 Hz), 2.74 (t, 2 H, H-7, J=8.5 Hz)

step 3

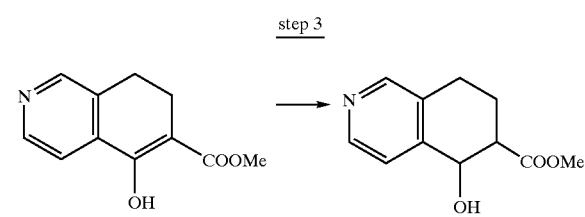

A solution of the enol from step 2 (350 mg, 1.71 mmol) in methanol (10 mL) was stirred in the presence of palladium on carbon (10%, 350 mg) under an atmosphere of hydrogen for 1 h. The catalyst was then removed by filtration through celite and., the filtrate was concentrated to dryness to give the desired compound as a white solid. (350 mg, 100%)

$^1$H NMR (400 MHz,DMSO) δ: 8.72 (s, 1 H, H-1), 8.67 (d, 1 H, H-3, J=5.8 Hz),), 7.90 (d, 1 H, H-4, J=5.8 Hz), 6.6 (br, 1 H, OH), 5.02 (d, 1 H, H-5, J=4.3 Hz), 3.63 (s, 3 H, $OCH_3$), 3.0 (m, 2 H), 2.8 (m, 1 H), 2.0 (m, 1 H), 1.9 (m, 1 H).

Step 4

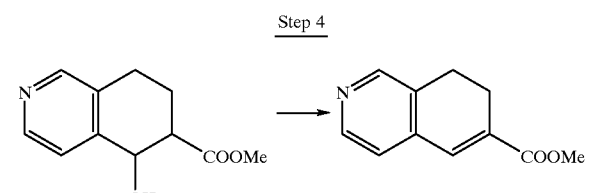

Methanesulfonyl chloride (0.18 ML, 2.37 mmol) was added to a solution of alcohol from step 3 (350 mg, 1.69 mmol) and triethylamine (0.35 mL, 2.54 mmol) in dichloromethane (10 mL) at 0° C. The mixture was then stirred at room temperature for 2 h and the solution was then washed with water, $NaHCO_3$ and dried using $Na_2SO_4$. The solvent was then removed and the residue was taken into dichloroethane (5 mL) and treated with DBU (1,8-diazabicyclo [5.4.0]undec-7-ene) (0.5 mL). The solution was stirred for 2 h at room temperature and the solvent was removed under vacuo and the residue was purified by chromatography (1% MeOH in $CH_2Cl_2$) to give the desired compound (159mg, 50% from alcohol) $^1$H NMR (300 MHz,CDCl$_3$) δ: 8.46 (d, 1 H, H-3, J=4.4 Hz), 8.44 (s, 1 H, H-1), 7.44(s, 1 H, H-5), 7.06 (d, 1 H, H-4, J=4.4 Hz), 3.83 (s, 3 H, OCH$_3$), 2.87 (t, 2 H, H-8, J=8.0 Hz), 2.69 (t, 2 H, H-7, J=8.0 Hz).

Step 5

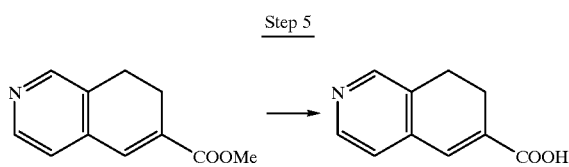

NaOH (1 N, 1.3 mL, 1.3 mmol) was added to a solution of ester from step 4 (159 mg, 0.84 mmol) in dioxane (3 mL) at rt. After 3 h, the mixture was concentrated to about 1 mL and HCl (6N) was carefully added to the ice cold solution until pH5 was reached. The resulting precipitate was collected, washed with water and dried under vacuo. (92 mg, 62%)

$^1$H NMR (400 MHz,DMSO) δ: 8.42 (m, 2 H, H-1 and H-3), 7.45 (s, 1 H, H-5), 7.31 (d, 1 H, H-4, J=4.9 Hz), 2.82 (t, 2 H, H-8, J=8.2 Hz), 2.53 (t, 2 H, H-7, J=7.5 Hz).

Step 6

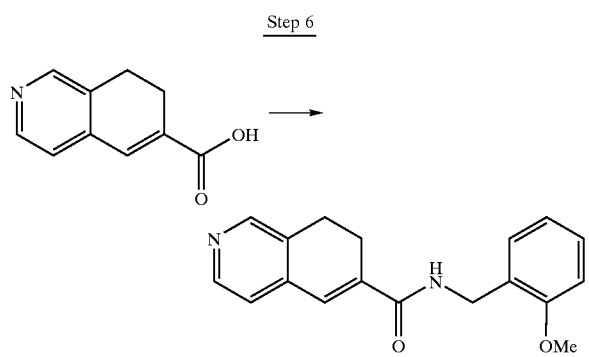

A solution of the acid from step 5 (60 mg, 0.34 mmol), 1-(3-dimethylaminopropyl)-3-ethylcarbodiimide hydrochloride (79 mg, 0.41 mmol), and HOBT (1-hydroxybenzotriazole hydrate) (55 mg, 0.41 mmol) 2-methoxybenzylamine (54 μL, 0.41 mmol) in DMF (1 mL) was stirred at room temperature for 24 h. The solvent was then removed under vacuo and the residue was purified by-chromatography eluting with 50–100 EtAC in Hexanes. The desired compound was obtained as a white solid. (80 mg, 79%)

$^1$H NMR (300 MHz, CDCl$_3$) δ: 8.45 (d, 1 H, J=4.8 Hz), 8.41 (s, 1 H, H-1), 7.31 (m, 2 H), 7.10 (s, 1 H, H-5), 7.03 (d, 1 H, H-4, J=4.8 Hz)6.94 (br, 1 H, NH), 4.59 (d, 2 H, CH$_2$, J=5.8 Hz), 3.91 (s, 3 H, OCH$_3$), 2.88 (t, 2 H, H-8, J=8.0 Hz), 2.64 (t, 2 H, H-7, J=8.3 Hz).

Compound #33
8-bromo-[1,6]Naphthyridine-2-carboxylic acid 2-N-ethylaminobenzylamine step 1

N-ethyl-2-aminobenzonitrile

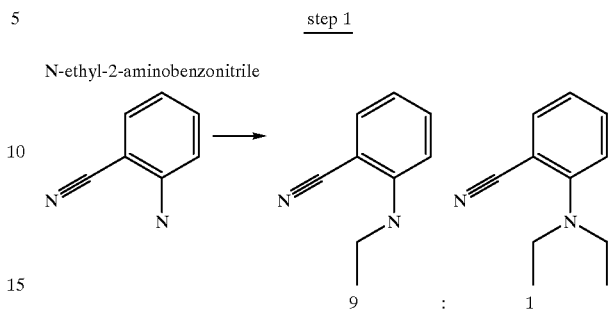

A solution of lithium bis(trimethylsylil)amide (7.6 mL, 1 M in tetrahydrofurane) is added to a cold (0° C.) solution of 2-aminobenzonitrile (1 g, 8.5 mmol) in tetrahydrofuran (10 mL) and DMF (2 mL). The resulting solution is stirred for 30 minutes, iodoethane (0.68 mL, 8.5 mmol) was then added dropwise. The solution is allowed to reach room temperature and stirred over night. The reaction mixture was then quenched with saturated $NH_4$ Cl evaporated, diluted with $CH_2Cl_2$, washed with water, brine and the combined organic extracts were dried with $Na_2SO_4$ and concentrated. The resulting liquide was chromatographed onto silica gel (30% EtOAc-Hex), giving the title compound in a 9 to 1 ratio of mono and bis alkylated compounds non separable.
N-ethyl-2-aminobenzonitrile:
$^1$H NMR (400 MHz)(CDCl$_3$) d: 7.41–7.33 (m, 2H, Ph), 6.68–6.65 (m, 2H, Ph), 4.5 (s, 1H, NH), 3.29–3.22 (m, 2H, CH$_2$N), 1.32(t, J=7 Hz, 3H, CH$_3$CH$_2$)
N-diethyl-2-aminobenzonitrile:
$^1$H NMR (400 mhz)( CDCl$_3$) d: 7.41–7.33 (m, 2H, Ph), 6.68–6.65 (m, 2H, Ph), 4.5 (s, 1 H, NH), 3.41 (q, 4H, CH$_2$N), 1.20(t, J=7 Hz, 6H, CH$_3$CH$_2$)

step 2

N-ethyl-2-aminobenzylamine dihydrochloride and
N-diethyl-2-aminobenzamine dihydrochloride

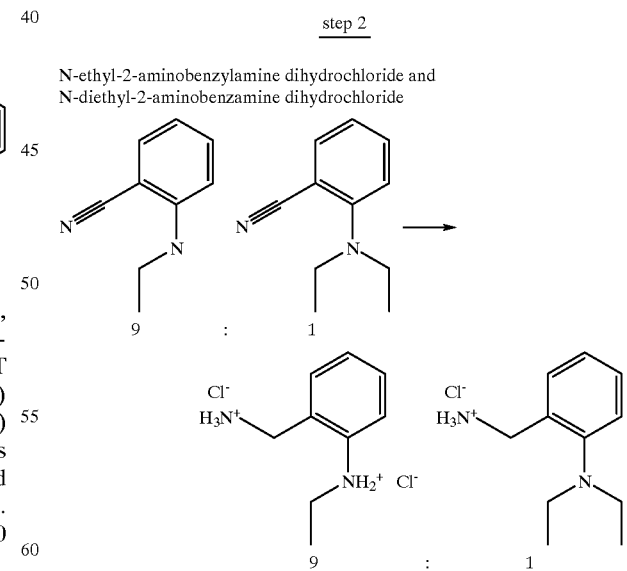

N-ethyl-2-aminobenzonitrile (0.4g, 2.7 mmol), 10% Pd/C (100 mg) is added in a dry flask followed by ethanol (15 mL). To this solution HCl was added (2.7 mL, 4 M in dioxane). The resulting reaction was placed under an H$_2$(g) atmosphere. The resulting solution was filtered over celite, was evaporated, triturated with ether, and the solvent was evaporated to yield the above intermediate.

N-ethyl-2-aminobenzylamine dihydrochloride:
¹H NMR (400 MHz)(DMSO) d: 8.5–8.2 (m, 3H, NH₃), 7.35–7.25 (1, 2H, Ph), 7.34(t, J=7.5 Hz, 1 H, Ph) 7.1–6.9 (m, 2H, Ph), 4.07 (s, 2H, CH₂N), 3.19 (q, 2H, J=7 Hz, CH₃CH₂), 1.27(t, J=7 Hz, 3H, CH₃CH₂)

N-diethyl-2-aminobenzamine dihydrochloride:
¹H NMR (400 MHz)(DMSO) d: 8.5–8.2 (m, 3H, NH₃), 7.35–7.25 (1, 2H, Ph), 7.34(t, J=7.5 Hz, 1H, Ph) 7.1–6.9 (m, 2H, Ph), 4.07 (s, 2H, CH₂N), 3.33 (q, 2H, J=7 Hz, CH₃CH₂), 1.07(t, J=7 Hz, 3H, CH₃CH₂)

step 3

8-bromo-[1,6]Naphthyridine-2-carboxylic acid

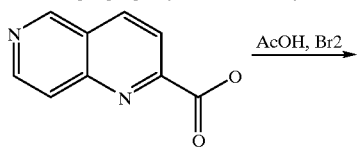
AcOH, Br2

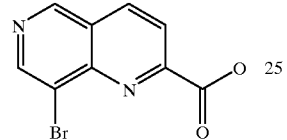

is added Br₂ over 40 minutes to a suspension of the [1,6]Naphthyridine-2-carboxylic acid (3 g,17.25 mmol) in acetic acid (150 mL) at room temperature (18.96 mmol). The solution was stirred over night at room temperature then the mixture was quenched with ice and stirred for 1 hour. The suspension was evaporated to dryness then triturated, filtrated and washed with a minimum of cold water. The resulting composition was dried under vacuum over night to yield the title compound in a 59% yield.

¹H NMR (400 MHz)(DMSO) d: 14.1–13.8 (M, 1H, COOH), 9.49 (s, 1H, H5), 9.10 (s, 1 H, H7), 8.83 (d, 1H, J=8.5 Hz, H4), 8.31 (d, 1H, J=8.5 Hz, H3)

step 4

8-bromo-[1,6]Naphthyridine-2-carboxylic acid 2-N-ethylamino-benzylamine

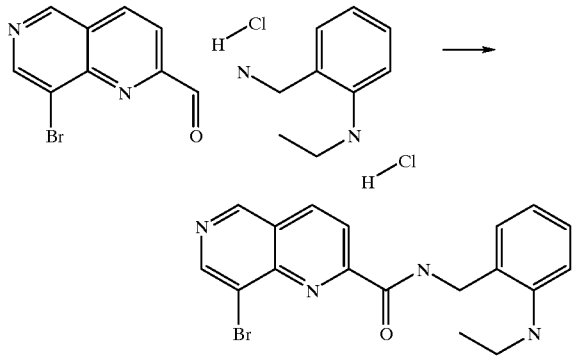

Triethylamine (0.095 mL, 0.68 mmol) was added to a solution of the salt (57 mg, 0.255 mmol) in DMF (1.5 mL) at room temperature. The solution was stirred for five minutes. Simultaneously, the acid (30 mg, 0.12 mmol), HOBT (25 mg, 0.19 mmol) and EDCI were added (36 mg, 0.19 mmol) The reaction was left to stir over night at room temperature. The solution was evaporated to dryness and the residue was dissolved in a minimum of CH₂Cl₂ and purified using flash chromatography ( 50% AcOEt/Hexane to 100% AcOEt) to yield the title compound in a 61% yield.

¹H NMR (400 MHz)(CDCl₃) d: 9.27 (s, 1H, H5), 9.05 (s, 1H, H7), 8.65–8.55 (s, 1H, NH), 8.55–8.45 (m, 2H, H4 and H3), 7.3–7.2 (m, 2H, Ph), 7.85–7.65 (m, 2H, Ph), 4.67 (d, 2H, J=6.5 Hz, CH₂), 3.25–3.15 (m, 2H, CH₂CH₃), 1.4–1.3 (m, 3H, CH₃CH₂)

step 5

8-bromo-[1,6]Naphthyridine-2-carboxylic acid 2-N-ethylaminobenzylamine hydrochloride salt

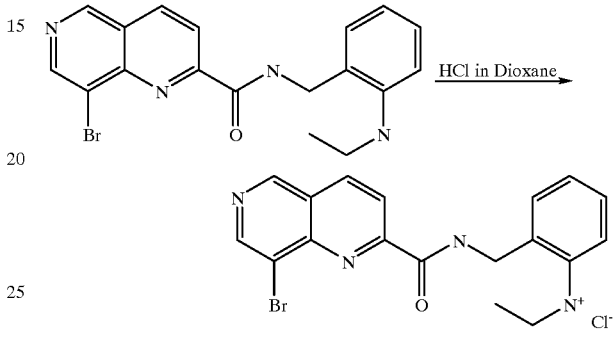

HCl was added to a solution of the amide (28.4 mg, 0.06 mmol) in CH₂Cl₁₂ (0.5 mL) at room temperature (1 mL, 4 M in dioxane). The solution was stirred for 20 minutes at room temperature. The suspension was evaporated to dryness then triturated in ether to yield the title compound in a quantitative yield.

¹H NMR (400 MHz)(CDCl₃) d: 9.27 (s, 1H, H5), 9.05 (s, 1H, H7), 8.65–8.55 (s, 1H, NH), 8.55–8.45 (m, 2H, H4 and H3), 7.3–7.2 (m, 2H, Ph), 7.85–7.65 (m, 2H, Ph), 4.67 (d, 2H, J=6.5 Hz, CH₂), 3.25–3.15 (m, 2H, CH₂CH₃),1.4–1.3 (m, 3H, CH₃CH₂)

Compound #39
[1,6]Naphthyridine-2-thiocarboxylic acid-2-trifluoromethylbenzylamine;

Lawesson's reagent was added to a stirring solution of BCH-5024 (30 mg, 0.09 mmol) in toluene(1.5 mL) (38 mg, 0.09 mmol). The solution was then heated to 90° C. for 1 h. The solvent was evaporated and the product was purified by flash chromatography (50% AcOEt/He to 100% AcOEt) to yield 25.8 mg of the thioamide derivative.

¹H NMR (400MHz, CDCl₃): 10.55 (bs, 1H), 9.3 (s, 1H), 9.0 (d, J=8.5 Hz, 1H), 8.81 (d, J=6Hz, 1H), 8.44 (d, J=8.5 Hz, 1H), 7.90 (d, J=6.0 Hz, 1H), 7.75 (d, J=7.5 Hz, 1H), 7.68 (d, J=7.5 Hz, 1H), 7.56 (t, J=7.5Hz, 1H), 7.46 (t, J=7.5Hz, 1H), 5.37 (d, J=6 Hz, 2H).

Compound #46
1-(2-iso-propoxy-phenyl)-3-[1,6]naphthyridin-2-yl-urea;

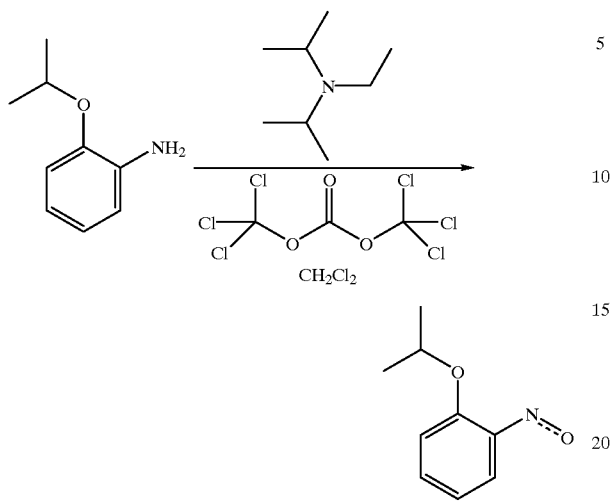

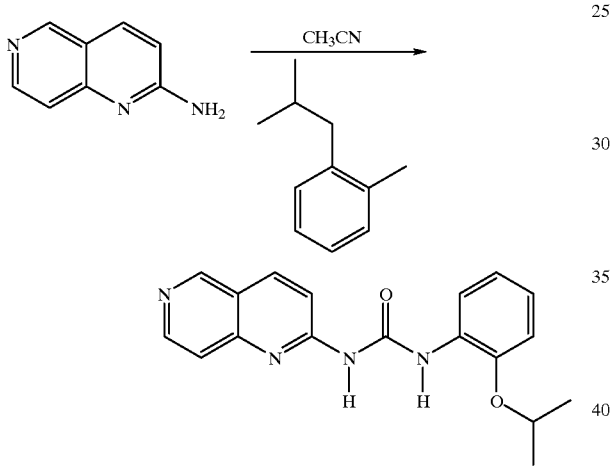

A solution of 2-isopropoxyphenylamine (400 mg, 2.64 mmol) and N,N-diisopropylethylamine (1.02 ml, 5.82 mmol) in dichloromethane (10.0 mL) was added dropwise via cannula to a solution of triphosgene (274.7 mg, 0.93 mmol) in dichloromethane (6.0 mL) at −78° C. The solution was stirred at −78° C. for 1 hour, then at 0° C. for 1 hour, and then at room temperature for 1 hour. The mixture was concentrated, triturated with pentane, and then filtered. The desired isocyanate was isolated as a brown oil (449.7 mg, 96%): $^1$H NMR (400 MHz, CDCl$_3$) δ 7.12 (1H, Ph), 6.99 (1H, Ph), 6.90 (1H, Ph), 6.86 (1H, Ph), 4.65 (septet, 1H, CH, J 6.5 Hz), 1.42 (d, 6H, CH$_3$, J 6.5 Hz) ppm. A mixture of the isocyanate (45.8 mg, 0.258) and the amine (25 mg, 0.172) in acetonitrile (1 mL) was heated at reflux for 3 hours. The solvent was removed using a roto-evaporator. The residue was then triturated with diethyl ether, filtered, and washed with diethyl ether. The solid was washed again with ethanol and then diethyl ether repeatedly. The desired product was isolated as a light brown solid (34.4 mg, 62%): m.p.>200° C.

$^1$H NMR (400 MHz, DMSO) δ 11.33 (bs, 1H, NH), 10.56 (bs, 1H, NH), 9.17 (s, 1H, H-5), 8.68 (d, 1H, H-7, J 5.8 Hz), 8.43 (d, 1H, H-4, J 8.9 Hz), 8.16 (1H, Ph), 7.68 (d, 1H, H-8, J 5.8 Hz), 7.50 (d, 1H, H-3, J 8.9 Hz), 7.12 (1H, Ph), 7.03 (1H, Ph), 6.93 (1H, Ph), 4.70 (septet, 1H, CH, J 6.0 Hz), 1.34 (d, 6H, CH$_3$, J 6.0 Hz) ppm.

Compound #63
8-(vinyl)-[1,6]Naphthyridine-2-carboxylic acid 2-isopropoxybenzylamine

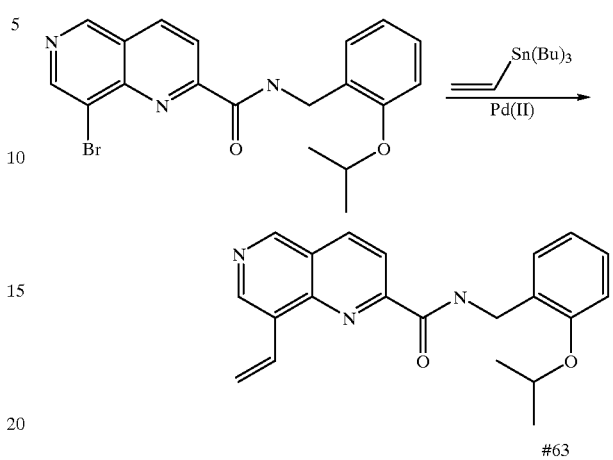

To a mixture of the bromide (0.05 mg, 0.125 mmol), vyniltributyltin (0.047 mL, 0.1625 mmol), Bis (triphenylphosphine)Pd(II)dichloride (7 mg, 0.01 mmol) add DMF (1 mL) and heat at 120° C. for 1 hours. The solution is evaporated to dryness and the residue is dissolved in a minimum of CH$_2$Cl$_2$ and purified using flash chromatography (100% He to 100% AcOEt).

$^1$H NMR (400 MHz)(DMSO) d: 9.25 (s, 1H), 9.00 (s, 1H), 8.73 (m, 1H), 8.48 (d, J=8.5Hz, 1H), 8.44 (d, J=8.5Hz, 1H), 7.80 (dd, J=11.5, 17.5Hz, 1H), 7.40 (d, 1H, J=7.5 Hz), 7.3–7.2 (m, 1H), 6.95–6.91 (m, 2H), 6.12 (d, 1H, J=17.5 Hz), 5.59 (d, J=11.5 Hz, 1H), 4.73 (d, J=6.5 Hz, 1H), 4.74–4.68 (m, 1H), 1.46 (d, J=6 Hz, 1H),

Compound #64
8-(methyl)-[1,6]Naphthyridine-2-carboxylic acid 2-isopropoxybenzylamine

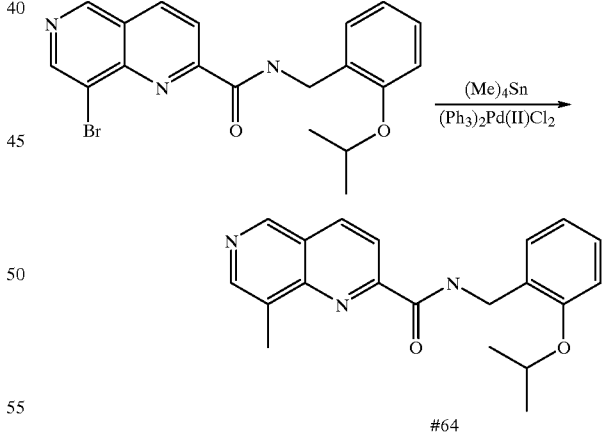

To a mixture of the bromide (156.8 mg, 0.39 mmol), tretramethyltin (0.22 mL, 1.56 mmol), Bis (triphenylphosphine)Pd(II)dichloride (42 mg, 0.06 mmol) add DMF (3 mL) seal the flask with a glass stopper and heat at 80° C. for 24 hours. The solution is evaporated to dryness and the residue is dissolved in a minimum of CH$_2$Cl$_2$ and purified using flash chromatography (50% AcOEt/He to 100% AcOEt).

$^1$H NMR (400 MHz)(DMSO) d: 9.20 (s, 1H), 8.71 (m, 1H), 8.67 (s, 1H), 8.47 (d, J=8.5 Hz, 1H), 8.43 (d, J=8.5 Hz,

1H), 7.41 (d, 1H, J=7 Hz), 7.28–7.25 (m, 1H), 6.94-6.90 (m, 2H), 4.74 (d, J=6.5 Hz, 1H), 4.72–4.66 (m, 1H), 2.77 (s, 3H), 1.44 (d, J=6 Hz, 1H),

Compound #65

(S)-(+)-8-Bromo-[1,6]Napthyridine-2-Carboxylic Acid 2-Sec-Butoxy-Benzylamide

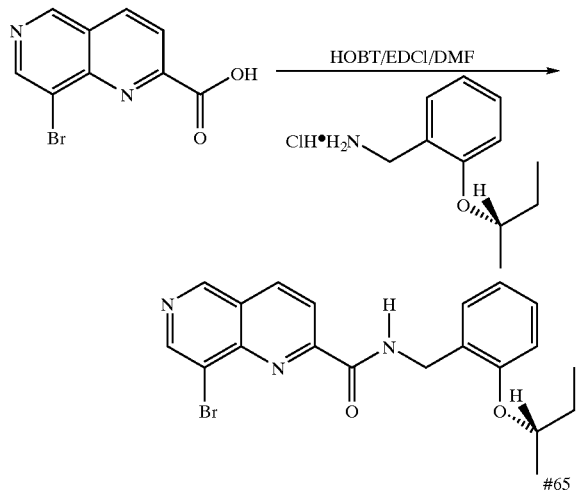

To a stirring solution of hydrochloride salt (74.7 mg, 0.346 mmol) in anhydrous DMF (1.0 mL) was added triethylamine (48.2 μL, 0.346 mmol). After 5 minutes, the 2-[1,6]naphthyridinecarboxylic acid (73.0 mg, 0.288 mmol), 1-hydroxybenzotriazole hydrate (42.9 mg, 0.317 mmol), and 1-(3-dimethylaminopropyl)-3-ethylcarboiimide hydrochloride (62.0 mg, 0.317 mmol) were added sequentially. The resulting mixture was allowed to stir at RT overnight. The solvent was removed under vacuum. Flash column chromatography of the residue (50% hexane/ethyl acetate) afforded the desired product as a white solid (106.6 mg, 89%): m.p. 78–80° C.

Compound #66

8-Bromo-[1,6]naphthyridine-2-carboxylic acid (1-phenyl-ethyl)-amide

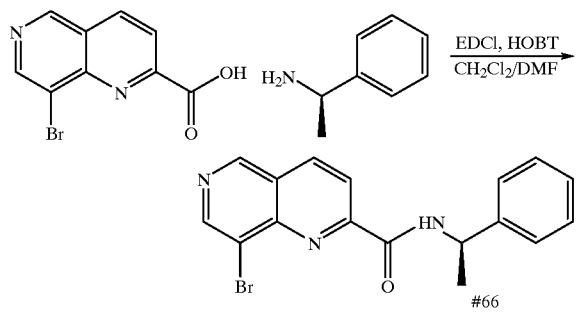

This compound was prepared following the scheme disclosed for synthesis of Compound #33.

¹H NMR (400 MHz, CDCl₃): 9.27 (s, 1H), 9.06 (s, 1H), 8.64 (d, J=6.6 Hz, 1H), 8.50 (2d, J=8.5 Hz, 2H), 7.40 (m, 5H), 5.38 (m, 1H), 1.71 (d, J=6.9 Hz, 3H).

Compound #67

7,8-Dihydro-isoquinoline-6-carboxylic acid phenethyl-amide

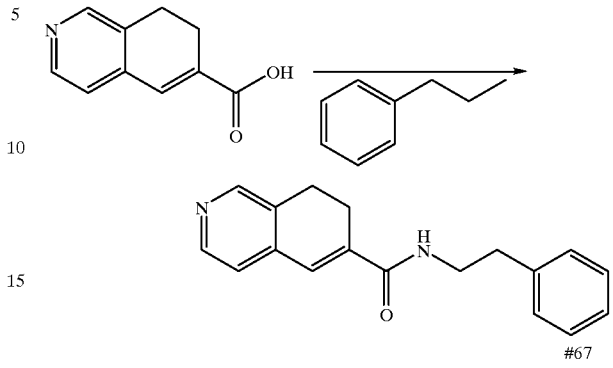

To a stirring mixture of the acid (40 mg, 0.228 mmol) in anhydrous DMF (1.0 mL) at RT was added sequencially 1-hydroxybenzotriazole hydrate (33.9 mg, 0.251 mmol), the amine (43.4 μL, 0.342 mmol) and 1-(3-dimethylaminopropyl)-3-ethylcarboiimide hydrochloride (49.1 mg, 0.251 mmol). The resulting mixture was allowed to stir at RT overnight. The solvent was removed under vacuum. Flash column chromatography of the residue (100% ethyl acetate) afforded the desired product as a white solid (50.5 mg, 80%).

Compound #68

7,8-Dihydro-isoquinoline-6-carboxylic acid [2-(1H-indol-3-yl)-ethyl-amide

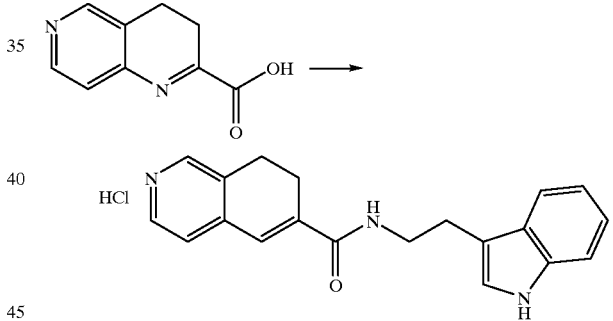

To a suspension of 7,8-dihydroisoquinoline-6-carboxylic acid (50 mg, 0,29 mmol) inTHF 92 mL) at 0° C. was added N-methyl morpholine (96 μL, 0.87 mmol) followed by isopropyl chloroformate (1 M in toluene, 0.29 mL, 0.29 mmol) After 1 h at 0° C., tryptamine hydrochloride (62 mg, 0.31 mmol) was added>the mixture was then allowed to warm to room temperature and stirred for 2 h. NaOH 91 N, 1 mL0 was added and the product was extracted into metyhylene chloride. After drying the solution (Na₂SO₄) and removal of solvent, the resulting solid was triturated with ether. The solid was then dissolved in methylene chloride (5 mL) and HCL (4 N in dioxane, 1 mL) was added. The volatiles were removed and the solid was triturated with ether and dried under vacuo. (69 mg, 68%)

¹H NMR (400 MHz, DMSO) δ: 10.84 (s, 1 H, H-5), 8.70 (m, 2H), 8.56 (t, 1 H, NH), 7.79 (d, 1 H, J=5.7 Hz), 7.56 (d, 1 H, J=7.6 Hz), 7.34 (m, 2 H), 7.19 (s, 1 H), 7.06 (t, 1 H, J=7.6 Hz), 6.98 (t, 1 H, J=7.6 Hz), 3.44 (m, 2 H), 2.99 (t, 2 H, J=8.3 Hz), 2.91 (t, 2 H, J=7.6 Hz), 2.64 (t, 2 H, J=8.2 Hz)

In a like manner, the following compounds were prepared:

Compound #22 N-(2-hydroxybenzyl)-2-(1,6) naphthyridine-carboxamide;

Compound #23 N-(2-methoxycarbonylbenzyl)-2-(1,6)-naphthyridinecarboxamide;

Compound #26 N-(2propoxybenzyl)-2-[1,6] naphthyridine-2-carboxamide;

Compound #27 (2-{[([1,6]naphthyridine-2-carbonyl)-amino]-methyl}-phenyl)-carbonic acid tert-butyl ester;

Compound #28 [1,6]Naphthyridine-2-carboxylic acid (2,3,4,5-tetrahydrobenzo[B]oxepin-5-yl)-amide;

Compound #29 [1,6]Naphthyridine-2-carboxylic acid (chroman-4-yl)-amide;

Compound #30 N-(2'-methoxybenzyl)-5-amino-2-[1,6] naphthyridinecarboxamide;

Compound #31 [1,6]Naphthyridine-2-carboxylic acid 2,3-(methylenedioxy)-benzylamide Compound #33 8-bromo-[1,6]naphthyridine-2-carboxylic acid (2-N-ethylaminobenzylamine);

Compound #34 8-bromo-[1,6]naphthyridine-2-carboxylic acid (2-isopropoxybenzylamine);

Compound #35 8-bromo-[1,6]naphthyridine-2-carboxylic acid (2-methoxybenzylamine);

Compound #36 8-chloro-[1,6]naphthyridine-2-carboxylic acid (2-isopropoxybenzylamine);

Compound #37 8-chloro-[1,6]naphthyridine-2-carboxylic acid (2-N-ethylaminobenzylamine);

Compound #38 8-(2pyridyl)-[1,6]naphthyridine-2-carboxylic acid (2--isopropoxybenzylamine);

Compound #40 [1,6]Naphthyridine-2-thiocarboxylic acid-2-isopropoxybenzylamine;

Compound #41 [1,6]Naphthyridine-2-thiocarboxylic acid-3-methoxybenzylamine;

Compound #42 8-bromo-[1,6]Naphthyridine-2-thiocarboxylic acid-2-isopropoxybenzylamine;

Compound #43 [1,6]Naphthyridine-2-thiocarboxylic acid 2-methoxy-benzylamide;

Compound #44 [1,6]Naphthyridine-2-thiocarboxylic acid 2-ethoxy-benzylamide;

Compound #45 [1,6]Naphthyridine-2-thiocarboxylic acid-2-methoxy-cyclohexylmethyl-amide;

Compound #47 1-(2-iso-propoxybenzyl)-3-[1,6] naphthyridin-2-yl-urea;

Compound #48 1-(N-boc-4-aminobutyl)-3-[1,6] naphthyridin-2-yl-urea;

Compound #49 1-(4-aminobutyl)-3-[1,6]naphthyridin-2-yl-urea hydrochloride;

Compound #50 1-[(S)-α-methylbenzyl]-3-[1,6] naphthyridin-2-yl-urea;

Compound #51 1-[(R)-α-methylbenzyl]-3-[1,6] naphthyridin-2-yl-urea;

Compound #52 1-(2-methoxy-phenyl)-3-[1,6] naphthyridin-2-yl-urea;

Compound #53 1-butyl-3-[1,6]naphthyridin-2-yl-urea;

Compound #54 1-(2-methoxybenzyl)-3-[1,6] naphthyridin-2-yl-urea;

Compound #55 1-(2-ethoxy-phenyl)-3-[1,6]naphthyridin-2-yl-urea;

Compound #56 1-(2-methyl-phenyl)-3-[1,6] naphthyridin-2-yl-urea;

Compound #57 8-(2-pyridyl)-[1,6]naphthyridine-2-carboxylic acid (2-isopropoxybenzylamine); and Compound #69 [1,6]Naphthyridine-2-Carboxylic Acid [2-(1h-Indol-3-Yl)-Ethyl]-Amide.

The following Compounds were obtained commercially (Peakdale Fine Chemicals Limited, Glossop Derbyshire, UK):

Compound #24 (1,6)naphthyridine-2-carboxylic acid allylamide (PFC-029);

Compound #25 N-(2-methoxybenzyl)-2-(1,6) naphthyridine-carboxamide (PFC-032).

EXAMPLE 2

Preparation Of Thiazolo[5,4-C]Pyridine Compounds

Compounds #58 and #59
[5,4-c]pyridine-2-carboxylic acid ethyl ester and thiazolo[5,4-c]pyridine-2-carboxylic acid-2-methoxybenzylamide

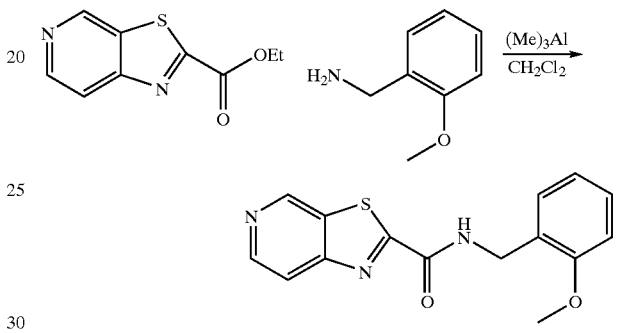

To a solution of thiazolo [5,4-c]pyridine-2-carboxylic acid ethyl ester (14 mg, 0.08 mmol) and 2-methoxy benzyl amine (0.03 mL, 0.23 mmol)in dichloromethane(0.3 mL) was added a solution of trimethylaluminum in hexane(0.115 mL, 2.0 M., 0.23 mmol). The solution was then stirred for 5 hours at room temperature. After usual work-up, the product was purified by flash chromatography (CH$_2$Cl$_2$/EtOAc 2:1) to give 14 mg of the thiazolo derivative.

$^1$H NMR (400 MHz, CDCl$_3$): 9.32 (s, 1H), 8.72 (d, J=6.0 Hz, 1H), 7.95 (d, J=6.0 Hz, 2H), 7.35 (bd, J=7.6 Hz, 2H), 7.35 (m,2H), 6.95 (m, 2H), 4.71 (d, J=6.0 Hz, 2H) 3.94 (s, 3H).

Compound #60
Thiazolo[5,4-c]pyridine-2-carboxylic acid-2-isopropoxybenzylamide

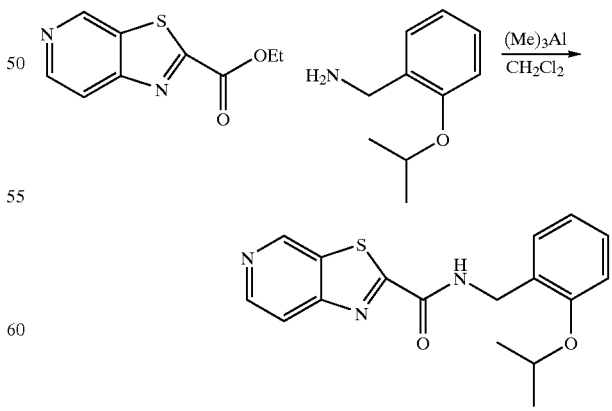

To a solution of thiazolo [5,4-c]pyridine-2-carboxylic acid ethyl ester (34 mg, 0.16 mmol) and 2-isopropoxy benzyl amine (67 mg, 0.41 mmol)in dichloromethane(1.7 mL) was added a solution of trimethylaluminum in hexane (0.203 mL, 2.0 M., 0.41 mmol). The solution was then stirred for 5 hours at room temperature. After usual work-up, the product was purified by flash chromatography (CH$_2$Cl$_2$/EtOAc 2:1) to give 30 mg of the thiazolo derivative.

$^1$H NMR (400 MHz, CDCl$_3$): 9.32 (s, 1H), 8.72 (d, J=6.0 Hz, 1H), 8.12 (bs, 1H), 7.93 (d, J=6.0 Hz, 2H), 7.35 (m, 2H), 6.95 (m, 2H), 4.69 (m, 2H) 1.45 (d, J=6 Hz, 6H).

Compound #61

Thiazolo[5,4-c]pyridine-2-carboxylic acid(1(R)-phenyl-ethyl)amide

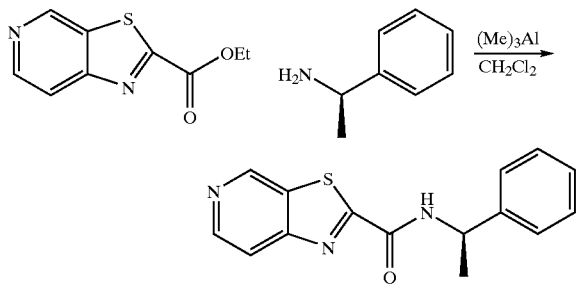

To a solution of thiazolo [5,4-c]pyridine-2-carboxylic acid ethyl ester (16 mg, 0.08 mmol) and 1(R)-phenyl ethyl amine (0.03 mL, 0.23 mmol) in dichloromethane(0.3 mL)was added a solution of trimethylaluminum in hexane (0.115 mL, 2.0 M., 0.23 mmol). The solution was then stirred for 5 hours at room temperature. After usual work-up, the product was purified by flash chromatography (CH$_2$Cl$_2$/EtOAc 1:1)and triturated in hexane to give 14 mg of the thiazolo derivative.

$^1$H NMR (400 MHz, CDCl$_3$): 9.33 (s, 1H), 8.73 (d, J=5.7 Hz, 1H), 7.95 (d, J=5.2 Hz, 1H), 7.70 (d, J=7.6 Hz, 1 H), 7.39 (m,5H), 5.35 (m, 1H), 1.70 (d, J=6.9 Hz, 3H).

Compound #62

Thiazolo[5,4-c]pyridine-2-carboxylic acid(1(S)-phenyl-ethyl)amide

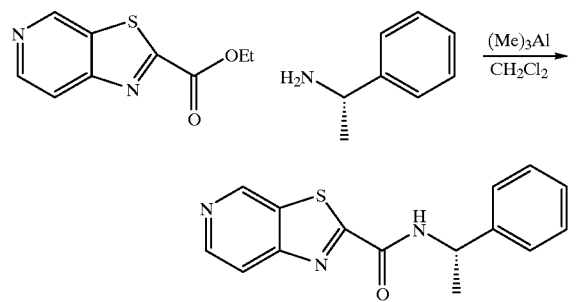

To a solution of thiazolo [5,4-c]pyridine-2-carboxylic acid ethyl ester (16 mg, 0.08 mmol) and 1(S)-phenyl ethyl amine (0.03 mL, 0.23 mmol)in dichloromethane(0.3 mL) was added a solution of trimethylaluminum in hexane(0.115 mL, 2.0 M., 0.23 mmol). The solution was then stirred for 5 hours at room temperature. After usual work-up, the product was purified by flash chromatography (CH$_2$Cl$_2$/EtOAc 1:1)and triturated in hexane to give 12 mg of the thiazolo derivative.

$^1$H NMR (400 MHz, CDCl$_3$): 9.33 (s, 1H), 8.73 (d, J=5.7 Hz, 1H), 7.95 (d, J=5.2 Hz, 1H), 7.70 (d, J=7.6 Hz, 1H), 7.39 (m,5H), 5.35 (m, 1H), 1.70 (d, J=6.9 Hz, 3H).

EXAMPLE 3

Antiviral Assays

The anti-HIV activity of test Compounds was evaluated according to standard procedures similar to those described in Ojwang et al (J. Acquired Immune Deficiency Syndromes, 1994,7:560).

Inhibition of other viruses was assayed according to standard techniques. The following general procedures were employed Inhibition of Viral Cytopathic Effect (CPE)

This test, run in 96-well flat-bottomed micro plates, is used for the initial antiviral evaluation of all new test Compounds. In this CPE inhibition test, seven one-half log$_{10}$ dilutions of each test Compound are added to 4 cups containing the cell monolayer; within 5 min., the virus is added and the plate sealed, incubated at 37° C. and CPE read microscopically when untreated infected controls develop a 3 to 4+ CPE (approximately 72 hr to 168 hr depending on the virus). A known positive control drug (ribavirin, HPMPA, acyclovir, ganciclovir, depending on the virus) is evaluated in parallel with test drugs in each test.

The data are expressed as 50% effective (virus-inhibitory) concentrations (EC50).

Neutral Red (NR) Dye Uptake

This test is run to validate the CPE inhibition seen in the initial test, and utilizes the same 96-well micro plates after the CPE has been read. Neutral red is added to the medium; cells not damaged by virus take up a greater amount of dye, which is read on a computerized microplate autoreader. An EC50 is determined from this dye uptake.

Plaque Reduction Assay (Cytomegalovirus)

Monolayers of cells in 24-well microplates are exposed to virus, and, while the virus is adsorbing, the plates are centrifuged at 2200 rpm for 30 min at room temperature to enhance viral plaque formation. Seven one-half log concentrations of test Compound are then added to 2 wells per dilution. The plates are incubated at 37° C. in a moist atmosphere of 5% CO$_2$ and 95% air until the plates are examined. The cells are observed microscopically for morphological changes due to cytotoxicity of the test Compound, with CC50 values determined, then the medium is aspirated and the cells stained by adding crystal violet in 10% buffered formalin. After staining, the plaques are counted using a dissecting microscope, with EC50 values determined.

Methods For Assay Of Cytotoxicity

A. Visual Observation

In the CPE inhibition test, two wells of uninfected cells treated with each concentration of test Compound are run in parallel with the infected, treated wells. At the time CPE is determined microscopically, the toxicity control cells are also examined microscopically for any changes in cell appearance compared to normal control cells run in the same plate. These changes may be enlargement, granularity, cells with ragged edges, a filmy appearance, rounding, detachment from the surface of the well, or other changes. These changes are given a designation of T (100% toxic), P$_{VH}$ (partially toxic-very heavy-80%), P$_H$ (partially toxic-heavy-60%), P (partially toxic-40%), P$_S$ (partially toxic-slight-20%), or 0 (no toxicity-0%), conforming to the degree of cytotoxicity seen. A 50% cell inhibitory (cytotoxic) concentration (CC50) is determined by regression analysis of these data.

B. Neutral Red Uptake

In the neutral red dye uptake phase of the antiviral test described above, the two toxicity control wells also receive neutral red and the degree of color intensity is determined spectrophotometrically. A neutral red CC50 (NRCC50) is subsequently determined.

Data Analysis

Each test Compound's antiviral activity is expressed as a selectivity index (SI), which is the CC50 divided by the EC50.

Special procedures

Except where noted, test Compounds will be solubilized in 100% DMSO at a concentration of 10 mg/ml, then diluted until DMSO is no longer toxic to the cells.

C. $^3$H Thymidine Uptake Assay

Flat bottom 96 well plates are plated with 5X10E3 Vero-34 cells/well and 1X10E4 Hs68 or Wi-38 cells/well respectively and incubated overnight at 37° C. and 5% $CO_2$/air. After incubation, the supernatant medium is removed and replaced with test Compound dilutions in 2% DMEM (150 ul). The cells are then incubated 48 hours in a 5% $CO_2$ incubator at 37° C.

50 μl/well of 10 uCi/ml solution of [3H]-methyl thymidine (specific activity of approx. 2Ci/mmol) is added to the culture medium and incubated overnight (18 hours) in a 5% $CO_2$ incubator at 37° C.

Cells are then collected onto a fiberglass filter (Printed Filtermat A 1450-421 Wallac) with a Tomtec cell harvester. Suspended cells are collected directly onto filter while for adherent cells, the medium is first removed, then the cells washed with PBS and trypsinized for 2–3 minutes (50 μl trypsin/well) before collecting.

Filters are dried for 1 hour at 37–40° C. and then placed into bags (1450-microbeta #1450-432 Wallac) with 4.5 ml of Betascint and counts obtained with Microbeta 1450 Wallac (protocol 1).

The percent of cell proliferation is determined by comparison to the control (no test Compound) and thereby establishing 50% inhibitory concentration is established.

TABLE 2

Antiviral Activity Against HSV-1, HSV-2, Respiratory Syncitial Virus (RSV) and Influenza A
($IC_{50}$ and $CC_{50}$ = μg/ml)

| Compound | HSV-1 | | HSV-2 | | RSV | | INFLUENZA A | |
|---|---|---|---|---|---|---|---|---|
| | $IC_{50}$ | $CC_{50}$ | $IC_{50}$ | $CC_{50}$ | $IC_{50}$ | $CC_{50}$ | $IC_{50}$ | $CC_{50}$ |
| #26 | 0.36 | 3.2 | 0.19 | 1.9 | 4 | 3 | 5.6 | 5.6 |
| #32 | 5.5 | 14 | 15 | 29.0 | 50 | 30 | 60 | 67 |
| #46 | >100 | >100 | nd | nd | >30 | 30 | >32 | 19 |
| #66 | 1.0 | 20.0 | nd | nd | 4 | 5 | 56 | 24 |
| #63 | nd | nd | nd | nd | 12 | 5 | 5.6 | 5.6 |
| #64 | 2 | 3.5 | nd | nd | 0.6 | 0.6 | 2.4 | 2.4 |
| #68 | 0.72 | 12 | 0.96 | 14 | 60 | 20 | 2.1 | 2.1 |
| #67 | 16 | >100 | 86 | >100 | >100 | 30 | >100 | >100 |

TABLE 3

Antiviral Activity Against Influenza B, Rhinovirus (RV), Parainfluenza and Adnovirus

| Compound | INFLUENZA B | | RV | | PARAINFLUENZA | | ADENOVIRUS | |
|---|---|---|---|---|---|---|---|---|
| | $IC_{50}$ | $CC_{50}$ | $IC_{50}$ | $CC_{50}$ | $IC_{50}$ | $CC_{50}$ | $IC_{50}$ | $CC_{50}$ |
| #26 | 3.2 | 5.6 | <0.01 | 4 | 4 | 2 | 4 | 3 |
| #32 | 56 | nd | 10 | 25 | 100 | 20 | >100 | 80 |
| #46 | >32 | >22 | 1 | >30 | >30 | 30 | >30 | >30 |
| #66 | 18 | 18 | 0.3 | 3 | 83 | 10 | 9 | 8 |
| #63 | 5.2 | 2.4 | 2 | 9 | 10 | 8 | 9 | 7 |
| #64 | 1.8 | 1.8 | >0.08 | 16 | 1 | 1 | 3 | 1 |
| #68 | 7.2 | 11 | 2 | 10 | 50 | 25 | 20 | 30 |
| #67 | >100 | >100 | >20 | 40 | 100 | 30 | >100 | 30 |

TABLE 4

Antiviral Activity Against $HIV_{ROJO}$ and $HIV_{TEKI}$
$IC_{50}$ and $CC_{50}$ = μg/ml

| | $HIV_{ROJO}$ (PBMC$_s$) | | $HIV_{TEKI}$ (PBMC$_s$) | |
|---|---|---|---|---|
| Compound | $IC_{50}$ | $CC_{50}$ | $IC_{50}$ | $CC_{50}$ |
| #26 | 4.1 | 6.0 | 0.3 | 6.0 |
| #32 | 45 | >64 | nd | >64 |
| #46 | 3.2 | >100 | 4.3 | >100 |
| #66 | 1.4 | 27.3 | 2.2 | 27.3 |
| #63 | 0.7 | 7.0 | 4.9 | 7.0 |
| #64 | 0.28 | 4.3 | 0.8 | 4.3 |
| #68 | 2.9 | 7.1 | nd | 7.1 |
| #67 | 8.6 | 74.7 | 41.2 | 74.7 |

TABLE 5

Antiviral Activity Against HCMV:
$IC_{50}$ and $CC_{50}$ μg/ml

| | HCMV μg/ml | |
|---|---|---|
| Compound No | $IC_{50}$ | $CC_{50}$ |
| #59 | ~10 | >12.5 < 25 |
| #60 | >0.1 < 1 | >12.5 < 25 |
| #61 | >1 < 10 | >50 < 100 |
| #62 | ~1 | >25 < 50 |

We claim:

1. A method of inhibiting virus replication other than cytomegalovirus (CMV) replication in a mammal comprising administering to said mammal an anti-viral amount of a compound of formula (I):

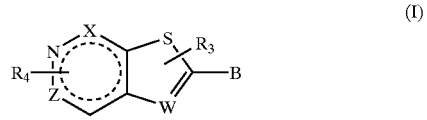
(I)

wherein

W is selected from N and $NR_5$; X and Z are independently selected from CH, $CR_4$, $CH_2$, C=O and $CHR_4$;

B is selected from the group consisting of:

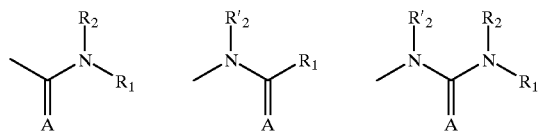

wherein, the ring containing X and Z is unsaturated;

A is O, N or S;

$R_1$ is selected from:

$C_{1-6}$ alkyl, $C_{2-6}$ alkenyl or $C_{3-7}$ cycloalkyl optionally substituted with OH, halogen amino, carboxyl, or saturated or unsaturated $C_{3-10}$ carbocycle or $C_{3-10}$ heterocycle optionally substituted with OH, halogen, amino, mercapto, carboxy, $C_{1-4}$ alkyl, $C_{1-4}$ alkoxy, $C_{1-4}$ alkylthio, $C_{1-4}$ acyl, $C_{1-4}$ acyloxy or $C_{1-4}$ alkoxycarbonyl optionally substituted with OH, halogen, amino or $C_{1-4}$ alkoxy;

$C_{3-7}$ cycloalkyl fused to $C_{6-10}$ aryl optionally substituted with OH, halogen, amino, mercapto, carboxy, $C_{1-4}$ alkyl, $C_{1-4}$ alkoxy, $C_{1-4}$ alkylthio, $C_{1-4}$ acyl, $C_{1-4}$ acyloxy or $C_{1-4}$ alkoxycarbonyl optionally substituted with OH, halogen, amino or $C_{1-4}$ alkoxy, and saturated or unsaturated $C_{3-10}$ (carbocycle or heterocycle) optionally substituted with OH, halogen, amino, mercapto, carboxy, $C_{1-4}$ (alkyl, alkoxy, alkylthio, acyl, acyloxy or alkoxycarbonyl) optionally substituted with OH, halogen, amino or $C_{1-4}$ alkoxy;

$R_2$ and $R'_2$ are independently selected from H, or $C_{1-4}$ alkyl or $R_1$ and $R_2$ together form a saturated or unsaturated 5 or 6 member heterocycle optionally fused to $C_{6-10}$ aryl or heteroaryl;

$R_3$ and $R_4$ are independently selected from H, OH, halogen, amino, cyano, $C_{1-6}$ alkyl, $C_{2-6}$ alkenyl, $C_{1-6}$ alkoxy, $C_{1-6}$ acyl, $C_{1-6}$ acyloxy or $C_{1-6}$ alkoxycarbonyl optionally substituted with OH, halogen, amino or $C_{1-4}$ alkoxy, and saturated or unsaturated $C_{3-10}$ carbocycle or $C_{3-10}$ heteroxcycle optionally substituted with OH, halogen, amino, mercapto, $C_{1-4}$ alkylthio, $C_{1-4}$ alkoxycarbonyl, halo-substituted $C_{1-4}$ alkyl or halo-substituted $C_{1-4}$ alkoxy, $C_{1-4}$ alkyl, $C_{1-4}$ alkoxy or carboxy;

$R_5$ is H, $C_{1-6}$ alkyl or $C_{1-6}$ acyl optionally substituted with OH, halogen, amino or $C_{1-4}$ alkoxy.

2. A compound according to formula (1) and pharmaceutical acceptable salts thereof:

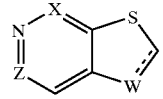
(1)

wherein

W is selected from N and $NR_5$; X and Z are independently selected from CH and $CR_4$ B is selected from the group consisting of:

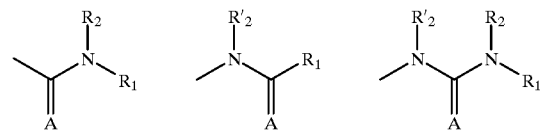

wherein,

A is O, N or S;

$R_1$ is selected from:

$C_{1-6}$ alkyl, $C_{2-6}$ alkenyl or $C_{3-7}$ cycloalkyl optionally substituted with OH, halogen amino, carboxyl, or saturated or unsaturated $C_{3-10}$ carbocycle or $C_{3-10}$ heterocycle optionally substituted with OH, halogen, amino, mercapto, carboxy, $C_{1-4}$ alkyl, $C_{1-4}$ alkoxy, $C_{1-4}$ alkylthio, $C_{1-4}$ acyl, $C_{1-4}$ acyloxy or $C_{1-4}$ alkoxycarbonyl optionally substituted with OH, halogen, amino or $C_{1-4}$ alkoxy;

$C_{3-7}$ cycloalkyl fused to $C_{6-10}$ aryl optionally substituted with OH, halogen, amino, mercapto, carboxy, $C_{1-4}$ alkyl, $C_{1-4}$ alkoxy, $C_{1-4}$ alkylthio, $C_{1-4}$ acyl, $C_{1-4}$ acyloxy or $C_{1-4}$ alkoxycarbonyl optionally substituted with OH, halogen, amino or $C_{1-4}$ alkoxy, and saturated or unsaturated $C_{3-10}$ (carbocycle or heterocycle) optionally substituted with OH, halogen, amino, mercapto, carboxy, $C_{1-4}$ (alkyl, alkoxy, alkylthio, acyl, acyloxy or alkoxycarbonyl) optionally substituted with OH, halogen, amino or $C_{1-4}$ alkoxy;

$R_2$ and $R'_2$ are independently selected from H, or $C_{1-4}$ alkyl or $R_1$ and $R_2$ together form a saturated or unsaturated 5 or 6 member heterocycle optionally fused to $C_{6-10}$ aryl or heteroaryl;

$R_3$ and $R_4$ are independently selected from H, OH, halogen, amino, cyano, $C_{1-6}$ alkyl, $C_{1-6}$ alkenyl, $C_{1-6}$ alkoxy, $C_{1-6}$ acyl, $C_{1-6}$ acyloxy or $C_{1-6}$ alkoxycarbonyl optionally substituted with OH, halogen, amino or $C_{1-4}$ alkoxy, and saturated or unsaturated $C_{3-10}$ carbocycle or $C_{3-10}$ heterocycle optionally substituted with OH, halogen, amino, mercapto, $C_{1-4}$ alkylthio, $C_{1-4}$ alkoxycarbonyl, halo-substituted $C_{1-4}$ alkyl or halo-substituted $C_{1-4}$ alkoxy, $C_{1-4}$ alkyl, $C_{1-4}$ alkoxy or carboxy;

$R_5$ is H, $C_{1-6}$ alkyl or $C_{1-6}$ acyl optionally substituted with OH, halogen, amino or $C_{1-4}$ alkoxy.

3. A compound according to claim 2 wherein A is O.

4. A compound according to claim 2, wherein B is

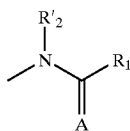

and $R_1$ is selected from benzyl, pyridinylmethyl or cyclohexylmethyl optionally substituted with one or two substituents selected from hydroxy; amino, $C_{1-4}$ alkyl, halogen, $C_{1-4}$ alkoxy, $C_{1-4}$ alkoxycarbonyl, $C_{1-4}$ alkylthio or $C_{1-4}$ halo-substituted alkyl.

5. A compound according to claim 2, wherein B is

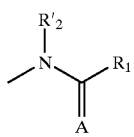

and $R_1$ is $C_{3-7}$ cycloalkyl fused to phenyl which is optionally substituted with one or two substituents selected from hydroxy, amino, $C_{1-4}$ alkyl, halogen, $C_{1-4}$ alkoxy, $C_{1-4}$ alkoxycarbonyl, $C_{1-4}$ alkylthio or $C_{1-4}$ halo-substituted alkyl.

6. A compound according to claim 2, wherein $R_2$ and $R'_2$ are independently selected from the group consisting of H and methyl.

7. A compound according to claim 2 wherein $R_4$ is H.
8. A compound according to claim 2 wherein $R_3$ is H.
9. A compound according to claim 2 wherein $R_5$ is H.
10. A compound according to claim 2 of formula (VIII):

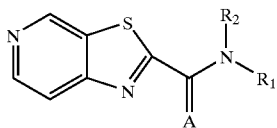

(VIII)

wherein
A is O or S
$R_1$ is selected from:
  $C_{1-6}$ alkyl, $C_{2-6}$ alkenyl or $C_{3-7}$ cycloalkyl optionally substituted with OH, halogen amino, carboxyl, or saturated or unsaturated $C_{3-10}$ carbocycle or $C_{3-10}$ heterocycle optionally substituted with OH, halogen, amino, mercapto, carboxy, $C_{1-4}$ alkyl, $C_{1-4}$ alkoxy, $C_{1-4}$ alkylthio, $C_{1-4}$ acyl, $C_{1-4}$ acyloxy or $C_{1-4}$ alkoxycarbonyl optionally substituted with OH, halogen, amino or $C_{1-4}$ alkoxy;
  saturated or unsaturated $C_{3-10}$ carbocycle or $C_{3-10}$ heterocycle optionally substituted with OH, halogen, amino, mercapto, carboxy, $C_{1-4}$ alkyl, $C_{1-4}$ alkoxy, $C_{1-4}$ alkylthio, $C_{1-4}$ acyl, $C_{1-4}$ acyloxy or $C_{1-4}$ alkoxycarbonyl optionally substituted with OH, halogen, amino or $C_{1-4}$ alkoxy; and
  $C_{3-7}$ cycloalkyl fused to $C_{6-10}$ aryl optionally substituted with OH, halogen, amino, mercapto, carboxy, $C_{1-4}$ alkyl, $C_{1-4}$ alkoxy, $C_{1-4}$ alkylthio, $C_{1-4}$ acyl, $C_{1-4}$ acyloxy or $C_{1-4}$ alkoxycarbonyl optionally substituted with OH, halogen, amino or $C_{1-4}$ alkoxy;
$R_2$ is selected from H, or $C_{1-4}$ alkyl.
11. A compound selected from:
Thiazolo[5,4-c]pyridine-2-carboxylic acid-2-methoxybenzylamide;
Thiazolo[5,4-c]pyridine-2-carboxylic acid-2-isopropoxybenzylamide;
Thiazolo[5,4-c]pyridine-2-carboxylic acid(1(R)-phenyl-ethyl)amide ;and
Thiazolo[5,4-c]pyridine-2-carboxylic acid(1(S)-phenylethyl)amide.
12. A method of inhibiting the replication of cytomegalovirus (CMV) in a mammal comprising administering to said mammal an anti-CMV amount of a compound according to formula (I) and pharmaceutical acceptable salts thereof:

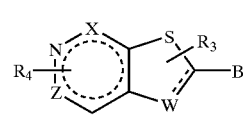

(I)

wherein
W is selected from N and $NR_5$; X and Z are independently selected from CH, $CR_4$, $CH_2$, C=O and $CHR_4$;
B is selected from the group consisting of:

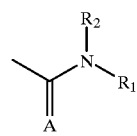 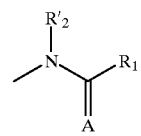 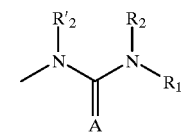

wherein,
the ring containing X and Z is unsaturated
A is O or S;
$R_1$ is selected from:
  $C_{1-6}$ alkyl, $C_{2-6}$ alkenyl or $C_{3-7}$ cycloalkyl optionally substituted with OH, halogen amino, carboxyl, or saturated or unsaturated $C_{3-10}$ carbocycle or $C_{3-10}$ heterocycle optionally substituted with OH, halogen, amino, mercapto, carboxy, $C_{1-4}$ alkyl, $C_{1-4}$ alkoxy, $C_{1-4}$ alkylthio, $C_{1-4}$ acyl, $C_{1-4}$ acyloxy or $C_{1-4}$ alkoxycarbonyl optionally substituted with OH, halogen, amino or $C_{1-4}$ alkoxy;
  $C_{3-7}$ cycloalkyl fused to $C_{6-10}$ aryl optionally substituted with OH, halogen, amino, mercapto, carboxy, $C_{1-4}$ alkyl, $C_{1-4}$ alkoxy, $C_{1-4}$ alkylthio, $C_{1-4}$ acyl, $C_{1-4}$ acyloxy or $C_{1-4}$ alkoxycarbonyl optionally substituted with OH, halogen, amino or $C_{1-4}$ alkoxy, and
  saturated or unsaturated $C_{3-10}$ (carbocycle or heterocycle) optionally substituted with OH, halogen, amino, mercapto, carboxy, $C_{1-4}$ (alkyl, alkoxy, alkylthio, acyl, acyloxy or alkoxycarbonyl) optionally substituted with OH, halogen, amino or $C_{1-4}$ alkoxy;
$R_2$ and $R'_2$ are independently selected from H, or $C_{1-4}$ alkyl or $R_1$ and $R_2$ together form a saturated for unsaturated 5 or 6 member heterocycle optionally fused to $C_{6-10}$ aryl or heteroaryl;
$R_3$ and $R_4$ are independently selected from H, OH, halogen, amino, cyano, $C_{1-6}$ alkyl, $C_{1-6}$ alkenyl, $C_{1-6}$ alkoxy, $C_{1-6}$ acyl, $C_{1-6}$ acyloxy or $C_{1-6}$ alkoxycarbonyl optionally substituted with OH, halogen, amino or $C_{1-4}$ alkoxy, and saturated or unsaturated $C_{3-10}$ carbocycle or $C_{3-10}$ heterxcycle optionally substituted with OH, halogen, amino, mercapto, $C_{1-4}$ alkylthio, $C_{1-4}$ alkoxycarbonyl, halo-substituted $C_{1-4}$ alkyl or halo-substituted $C_{1-4}$ alkoxy, $C_{1-4}$ alkyl, $C_{1-4}$ alkoxy or carboxy;

$R_5$ is H, $C_{1-6}$ alkyl or $C_{1-6}$ acyl optionally substituted with OH, halogen, amino or $C_{1-4}$ alkoxy.

13. A method according to claim 12 wherein A is O.
14. A method according to claim 12, wherein B is

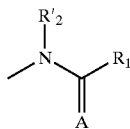

and $R_1$ is selected from benzyl, pyridinylmethyl or cyclohexylmethyl optionally substituted with one or two substituents selected from hydroxy; amino, $C_{1-4}$ alkyl, halogen, $C_{1-4}$ alkoxy, $C_{1-4}$ alkoxycarbonyl, $C_{1-4}$ alkylthio or $C_{1-4}$ halo-substituted alkyl.

15. A method according to claim 12, wherein B is

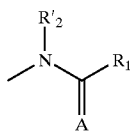

and $R_1$ is $C_{3-7}$ cycloalkyl fused to phenyl which is optionally substituted with one or two substituents selected from hydroxy, amino, $C_{1-4}$ alkyl, halogen, $C_{1-4}$ alkoxy, $C_{1-4}$ alkoxycarbonyl, $C_{1-4}$ alkylthio or $C_{1-4}$ halo-substituted alkyl.

16. A method according to claim 12, wherein $R_2$ and $R'_2$ are independently selected from the group consisting of H and methyl.
17. A method according to claim 12 wherein $R_4$ is H.
18. A method according to claim 12 wherein $R_3$ is H.
19. A method according to claim 12 wherein $R_5$ is H.
20. A method according to claim 12 of formula (VIII):

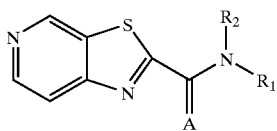

(VIII)

wherein

A is O $R_1$ is selected from:
  $C_{1-6}$ alkyl, $C_{2-6}$ alkenyl or $C_{3-7}$ cycloalkyl optionally substituted with OH, halogen amino, carboxyl, or saturated or unsaturated $C_{3-10}$ carbocycle or $C_{3-10}$ heterocycle optionally substituted with OH, halogen, amino, mercapto, carboxy, $C_{1-4}$ alkyl, $C_{1-4}$ alkoxy, $C_{1-4}$ alkylthio, $C_{1-4}$ acyl, $C_{1-4}$ acyloxy or $C_{1-4}$ alkoxycarbonyl optionally substituted with OH, halogen, amino or $C_{1-4}$ alkoxy;
  saturated or unsaturated $C_{3-10}$ carbocycle or $C_{3-10}$ heterocycle optionally substituted with OH, halogen, amino, mercapto, carboxy, $C_{1-4}$ alkyl, $C_{1-4}$ alkoxy, $C_{1-4}$ alkylthio, $C_{1-4}$ acyl, $C_{1-4}$ acyloxy or $C_{1-4}$ alkoxycarbonyl optionally substituted with OH, halogen, amino or $C_{1-4}$ alkoxy;
  $C_{3-7}$ cycloalkyl fused to $C_{6-10}$ aryl optionally substituted with OH, halogen, amino, mercapto, carboxy, $C_{1-4}$ alkyl, $C_{1-4}$ alkoxy, $C_{1-4}$ alkylthio, $C_{1-4}$ acyl, $C_{1-4}$ acyloxy or $C_{1-4}$ alkoxycarbonyl optionally substituted with OH, halogen, amino or $C_{1-4}$ alkoxy, and
  saturated or unsaturated $C_{3-10}$ (carbocycle or heterocycle) optionally substituted with OH, halogen, amino, mercapto, carboxy, $C_{1-4}$ (alkyl, alkoxy, alkylthio, acyl, acyloxy or alkoxycarbonyl) optionally substituted with OH, halogen, amino or $C_{1-4}$ alkoxy;

$R_2$ is selected from H, and $C_{1-4}$ alkyl.

21. A method according to claim 12 wherein the compound is selected from:
  Thiazolo[5,4-c]pyridine-2-carboxylic acid-2-methoxybenzylamide;
  Thiazolo[5,4-c]pyridine-2-carboxylic acid-2-isopropoxybenzylamide;
  Thiazolo[5,4-c]pyridine-2-carboxylic acid(1(R)-phenylethyl)amide and
  Thiazolo[5,4-c]pyridine-2-carboxylic acid(1(S)-phenylethyl)amide.

22. A compound according to claim 2 of formula (VIII):

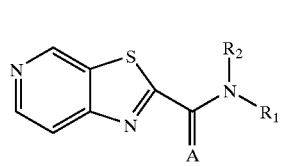

(VIII)

wherein

A is O $R_1$ is selected from:
  $C_{1-6}$ alkyl, $C_{2-6}$ alkenyl or $C_{3-7}$ cycloalkyl optionally substituted with OH, halogen amino, carboxyl, or saturated or unsaturated $C_{3-10}$ carbocycle or $C_{3-10}$ heterocycle optionally substituted with OH, halogen, amino, mercapto, carboxy, $C_{1-4}$ alkyl, $C_{1-4}$ alkoxy, $C_{1-4}$ alkylthio, $C_{1-4}$ acyl, $C_{1-4}$ acyloxy or $C_{1-4}$ alkoxycarbonyl optionally substituted with OH, halogen, amino or $C_{1-4}$ alkoxy;
  saturated or unsaturated $C_{3-10}$ carbocycle or $C_{3-10}$ heterocycle optionally substituted with OH, halogen, amino, mercapto, carboxy, $C_{1-4}$ alkyl, $C_{1-4}$ alkoxy, $C_{1-4}$ alkylthio, $C_{1-4}$ acyl, $C_{1-4}$ acyloxy or $C_{1-4}$ alkoxycarbonyl optionally substituted with OH, halogen, amino or $C_{1-4}$ alkoxy;
  $C_{3-7}$ cycloalkyl fused to $C_{6-10}$ aryl optionally substituted with OH, halogen, amino, mercapto, carboxy, $C_{1-4}$ alkyl, $C_{1-4}$ alkoxy, $C_{1-4}$ alkylthio, $C_{1-4}$ acyl, $C_{1-4}$ acyloxy or $C_{1-4}$ alkoxycarbonyl optionally substituted with OH, halogen, amino or $C_{1-4}$ alkoxy, and
  saturated or unsaturated $C_{3-10}$ (carbocycle or heterocycle) optionally substituted with OH, halogen, amino, mercapto, carboxy, $C_{1-4}$ (alkyl, alkoxy, alkylthio, acyl, acyloxy or alkoxycarbonyl) optionally substituted with OH, halogen, amino or $C_{1-4}$ alkoxy;

$R_2$ is selected from H, and $C_{1-4}$ alkyl.

* * * * *